United States Patent
Beeson, IV et al.

(10) Patent No.: US 11,578,338 B2
(45) Date of Patent: Feb. 14, 2023

(54) HEMIPTERAN ACTIVE INSECTICIDAL PROTEIN

(71) Applicant: Corteva Agriscience LLC, Indianapolis, IN (US)

(72) Inventors: William Beeson, IV, Indianapolis, IN (US); Jeffrey Church, Carmel, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 237 days.

(21) Appl. No.: 16/762,026

(22) PCT Filed: Oct. 29, 2018

(86) PCT No.: PCT/US2018/057899
§ 371 (c)(1),
(2) Date: May 6, 2020

(87) PCT Pub. No.: WO2019/094213
PCT Pub. Date: May 16, 2019

(65) Prior Publication Data
US 2020/0267993 A1  Aug. 27, 2020

Related U.S. Application Data

(60) Provisional application No. 62/583,684, filed on Nov. 9, 2017.

(51) Int. Cl.
*C12N 15/82* (2006.01)
*A01N 63/27* (2020.01)
*C07K 14/21* (2006.01)

(52) U.S. Cl.
CPC ......... *C12N 15/8286* (2013.01); *A01N 63/27* (2020.01); *C07K 14/21* (2013.01); *Y02A 40/146* (2018.01)

(58) Field of Classification Search
None
See application file for complete search history.

(56) References Cited

U.S. PATENT DOCUMENTS

2014/0007292 A1* 1/2014 Cerf .................. C12N 15/8286
435/254.11

OTHER PUBLICATIONS

Opota et al (2011, PLoS Pathogens 7(9): e1002259).*
Guo et al, 2004, Proc. Natl. Acad. Sci. USA 101: 9205-9210.*
UniProt Accession: A0A0F0FGL5, Jun. 24, 2015.
UniProt Accession: A0A0S4ICI8, Feb. 17, 2016.
UniProt Accession: A0A147GAX2, Jun. 8, 2016.
International Search Report and Written Opinion for International Application No. PCT/US18/57899, dated Jan. 22, 2019.

* cited by examiner

*Primary Examiner* — Anne Kubelik

(57) ABSTRACT

This disclosure concerns compositions and methods for novel pesticidal proteins, polynucleotides encoding such proteins, use of such novel pesticidal proteins to control Hemipteran/Lepidopteran plant pests, and transgenic plants that produce, and are protected, by these novel pesticidal proteins are described.

16 Claims, 8 Drawing Sheets
Specification includes a Sequence Listing.

Fig. 1

|  | 1 | 40 |
|---|---|---|
| IRDIG22274 (SEQ ID NO:4) | (1) MTIKEELGQPQSHSIELDEVSKEAASTRAALTSNLSGRFD | |
| PIP-1 (SEQ ID NO:3) | (1) MPIKEELSQPQSHSIELDDLKSEQGSLRAALTSNFAGNFD | |
| IRDIG37126 (SEQ ID NO:2) | (1) MTIKEDLSNPQSHSVELDQLHVGEVSAREALTANFAGSFD | |
|  | 41 | 80 |
| IRDIG22274 (SEQ ID NO:4) | (41) QYPTKKGDFAIDGYLLDYSSPKQGCWVDGITVYGDIYIGK | |
| PIP-1 (SEQ ID NO:3) | (41) QFPTKRGGFAIDSYLLDYSAPKQGCWVDGITVYGDIFIGK | |
| IRDIG37126 (SEQ ID NO:2) | (41) QFPTKSGSFEIDKYLLNYADPKQGCWLDGVTVYGDIYIGK | |
|  | 81 | 120 |
| IRDIG22274 (SEQ ID NO:4) | (81) QNWGTYTRPVFAYLQYVETISIPQNVTTTLSYQLTKGHTR | |
| PIP-1 (SEQ ID NO:3) | (81) QNWGTYTRPVFAYLQYMDTISIPQQVTQTRSYQLTKGHTK | |
| IRDIG37126 (SEQ ID NO:2) | (81) QNWGTYTRPVFAYLQHTDTISIPQQVTQTKSYQLSKGHTQ | |
|  | 121 | 160 |
| IRDIG22274 (SEQ ID NO:4) | (121) SFETSVNAKYSVGANIDIVNVGSEISTGFTRSESWSTTQS | |
| PIP-1 (SEQ ID NO:3) | (121) TFTTNVSAKYSVGGSIDIVNVGSDISIGFSNSESWSTTQT | |
| IRDIG37126 (SEQ ID NO:2) | (121) SFTKSVSAKYSVGGSIDIVNVSSDITVGFSSTEAWSTTQT | |
|  | 161 | 200 |
| IRDIG22274 (SEQ ID NO:4) | (161) FTDTTEMKGPGTFVIYQVVLVYAHNATSAGRQNANAFAYS | |
| PIP-1 (SEQ ID NO:3) | (161) FSNSTQLTGPGTFIVYQVVMVYAHNATSAGRQNGNAFAYN | |
| IRDIG37126 (SEQ ID NO:2) | (161) FTQSTELAGPGTFFVYQVVFVYAHNATSAGRQNGNAFAYS | |
|  | 201 | 240 |
| IRDIG22274 (SEQ ID NO:4) | (201) KTQAVGSRVDLYYLSAITQRKRVIVPSSNAVTPLDWDTVQ | |
| PIP-1 (SEQ ID NO:3) | (201) KTNTVGSRLDLYYLSAITQNSTVIVDSSKAIAPLDWDTVQ | |
| IRDIG37126 (SEQ ID NO:2) | (201) KTQQVDSRLDLYYLSAITQDRTVIVESSKAINPLDWDTVQ | |
|  | 241 | 271 |
| IRDIG22274 (SEQ ID NO:4) | (241) RNVLMENYNPGSNSGHFSFDWSAYNDPHRRY | |
| PIP-1 (SEQ ID NO:3) | (241) RNVLMENYNPGSNSGHFSFDWSAYNDPHRRY | |
| IRDIG37126 (SEQ ID NO:2) | (241) RNVLIENYNPASNSGHFRFDWSAYNDPHRRY | |

Fig. 6A

```
                                       1                                        40
              IRDIG37126 SEQIDNO:2   MTIKEDLSNPQSHSVELDQLHVGEVSAREALTANFAGSFD
         IRDIG37126_D18A SEQIDNO:15  MTIKEDLSNPQSHSVELAQLHVGEVSAREALTANFAGSFD
         IRDIG37126_D18S SEQIDNO:17  MTIKEDLSNPQSHSVELSQLHVGEVSAREALTANFAGSFD
     IRDIG37126_D18L_D75E SEQIDNO:23 MTIKEDLSNPQSHSVELLQLHVGEVSAREALTANFAGSFD
     IRDIG37126_D18Q_D75E SEQIDNO:24 MTIKEDLSNPQSHSVELQQLHVGEVSAREALTANFAGSFD
     IRDIG37126_D18R_D75E SEQIDNO:22 MTIKEDLSNPQSHSVELRQLHVGEVSAREALTANFAGSFD
         IRDIG37126_D18P SEQIDNO:16  MTIKEDLSNPQSHSVELPQLHVGEVSAREALTANFAGSFD
         IRDIG37126_D75A SEQIDNO:21  MTIKEDLSNPQSHSVELDQLHVGEVSAREALTANFAGSFD
          IRDIG37126_D6A SEQIDNO:13  MTIKEALSNPQSHSVELDQLHVGEVSAREALTANFAGSFD
         IRDIG37126_G23E SEQIDNO:18  MTIKEDLSNPQSHSVELDQLHVEEVSAREALTANFAGSFD
         IRDIG37126_H13A SEQIDNO:14  MTIKEDLSNPQSASVELDQLHVGEVSAREALTANFAGSFD
         IRDIG37126_R28K SEQIDNO:19  MTIKEDLSNPQSHSVELDQLHVGEVSAKEALTANFAGSFD
         IRDIG37126_R28M SEQIDNO:20  MTIKEDLSNPQSHSVELDQLHVGEVSAMEALTANFAGSFD 41                                       80
              IRDIG37126 SEQIDNO:2   QFPTKSGSFEIDKYLLNYADPKQGCWLDGVTVYGDIYIGK
         IRDIG37126_D18A SEQIDNO:15  QFPTKSGSFEIDKYLLNYADPKQGCWLDGVTVYGDIYIGK
         IRDIG37126_D18S SEQIDNO:17  QFPTKSGSFEIDKYLLNYADPKQGCWLDGVTVYGDIYIGK
     IRDIG37126_D18L_D75E SEQIDNO:23 QFPTKSGSFEIDKYLLNYADPKQGCWLDGVTVYGEIYIGK
     IRDIG37126_D18Q_D75E SEQIDNO:24 QFPTKSGSFEIDKYLLNYADPKQGCWLDGVTVYGEIYIGK
     IRDIG37126_D18R_D75E SEQIDNO:22 QFPTKSGSFEIDKYLLNYADPKQGCWLDGVTVYGEIYIGK
         IRDIG37126_D18P SEQIDNO:16  QFPTKSGSFEIDKYLLNYADPKQGCWLDGVTVYGSIYIGK
         IRDIG37126_D75A SEQIDNO:21  QFPTKSGSFEIDKYLLNYADPKQGCWLDGVTVYGAIYIGK
          IRDIG37126_D6A SEQIDNO:13  QFPTKSGSFEIDKYLLNYADPKQGCWLDGVTVYGDIYIGK
         IRDIG37126_G23E SEQIDNO:18  QFPTKSGSFEIDKYLLNYADPKQGCWLDGVTVYGDIYIGK
         IRDIG37126_H13A SEQIDNO:14  QFPTKSGSFEIDKYLLNYADPKQGCWLDGVTVYGDIYIGK
         IRDIG37126_R28K SEQIDNO:19  QFPTKSGSFEIDKYLLNYADPKQGCWLDGVTVYGDIYIGK
         IRDIG37126_R28M SEQIDNO:20  QFPTKSGSFEIDKYLLNYADPKQGCWLDGVTVYGDIYIGK 81                                       120
              IRDIG37126 SEQIDNO:2   QNWGTYTRPVFAYLQHTDTISIPQQVTQTKSYQLSKGHTQ
         IRDIG37126_D18A SEQIDNO:15  QNWGTYTRPVFAYLQHTDTISIPQQVTQTKSYQLSKGHTQ
         IRDIG37126_D18S SEQIDNO:17  QNWGTYTRPVFAYLQHTDTISIPQQVTQTKSYQLSKGHTQ
     IRDIG37126_D18L_D75E SEQIDNO:23 QNWGTYTRPVFAYLQHTDTISIPQQVTQTKSYQLSKGHTQ
     IRDIG37126_D18Q_D75E SEQIDNO:24 QNWGTYTRPVFAYLQHTDTISIPQQVTQTKSYQLSKGHTQ
     IRDIG37126_D18R_D75E SEQIDNO:22 QNWGTYTRPVFAYLQHTDTISIPQQVTQTKSYQLSKGHTQ
         IRDIG37126_D18P SEQIDNO:16  QNWGTYTRPVFAYLQHTDTISIPQQVTQTKSYQLSKGHTQ
         IRDIG37126_D75A SEQIDNO:21  QNWGTYTRPVFAYLQHTDTISIPQQVTQTKSYQLSKGHTQ
          IRDIG37126_D6A SEQIDNO:13  QNWGTYTRPVFAYLQHTDTISIPQQVTQTKSYQLSKGHTQ
         IRDIG37126_G23E SEQIDNO:18  QNWGTYTRPVFAYLQHTDTISIPQQVTQTKSYQLSKGHTQ
         IRDIG37126_H13A SEQIDNO:14  QNWGTYTRPVFAYLQHTDTISIPQQVTQTKSYQLSKGHTQ
         IRDIG37126_R28K SEQIDNO:19  QNWGTYTRPVFAYLQHTDTISIPQQVTQTKSYQLSKGHTQ
         IRDIG37126_R28M SEQIDNO:20  QNWGTYTRPVFAYLQHTDTISIPQQVTQTKSYQLSKGHTQ
```

Fig. 6B

```
                                  121                                      160
        IRDIG37126 SEQIDNO:2  SFTKSVSAKYSVGGSIDIVNVSSDITVGFSSTEAWSTTQT
   IRDIG37126_D18A SEQIDNO:15  SFTKSVSAKYSVGGSIDIVNVSSDITVGFSSTEAWSTTQT
   IRDIG37126_D18S SEQIDNO:17  SFTKSVSAKYSVGGSIDIVNVSSDITVGFSSTEAWSTTQT
IRDIG37126_D18L_D75E SEQIDNO:23 SFTKSVSAKYSVGGSIDIVNVSSDITVGFSSTEAWSTTQT
IRDIG37126_D18Q_D75E SEQIDNO:24 SFTKSVSAKYSVGGSIDIVNVSSDITVGFSSTEAWSTTQT
IRDIG37126_D18R_D75E SEQIDNO:22 SFTKSVSAKYSVGGSIDIVNVSSDITVGFSSTEAWSTTQT
   IRDIG37126_D18P SEQIDNO:16  SFTKSVSAKYSVGGSIDIVNVSSDITVGFSSTEAWSTTQT
   IRDIG37126_D75A SEQIDNO:21  SFTKSVSAKYSVGGSIDIVNVSSDITVGFSSTEAWSTTQT
   IRDIG37126_D6A  SEQIDNO:13  SFTKSVSAKYSVGGSIDIVNVSSDITVGFSSTEAWSTTQT
   IRDIG37126_G23E SEQIDNO:18  SFTKSVSAKYSVGGSIDIVNVSSDITVGFSSTEAWSTTQT
   IRDIG37126_H13A SEQIDNO:14  SFTKSVSAKYSVGGSIDIVNVSSDITVGFSSTEAWSTTQT
   IRDIG37126_R28K SEQIDNO:19  SFTKSVSAKYSVGGSIDIVNVSSDITVGFSSTEAWSTTQT
   IRDIG37126_R28M SEQIDNO:20  SFTKSVSAKYSVGGSIDIVNVSSDITVGFSSTEAWSTTQT 161                                      200
        IRDIG37126 SEQIDNO:2  FTQSTELAGPGTFFVYQVVFVYAHNATSAGRQNGNAFAYS
   IRDIG37126_D18A SEQIDNO:15  FTQSTELAGPGTFFVYQVVFVYAHNATSAGRQNGNAFAYS
   IRDIG37126_D18S SEQIDNO:17  FTQSTELAGPGTFFVYQVVFVYAHNATSAGRQNGNAFAYS
IRDIG37126_D18L_D75E SEQIDNO:23 FTQSTELAGPGTFFVYQVVFVYAHNATSAGRQNGNAFAYS
IRDIG37126_D18Q_D75E SEQIDNO:24 FTQSTELAGPGTFFVYQVVFVYAHNATSAGRQNGNAFAYS
IRDIG37126_D18R_D75E SEQIDNO:22 FTQSTELAGPGTFFVYQVVFVYAHNATSAGRQNGNAFAYS
   IRDIG37126_D18P SEQIDNO:16  FTQSTELAGPGTFFVYQVVFVYAHNATSAGRQNGNAFAYS
   IRDIG37126_D75A SEQIDNO:21  FTQSTELAGPGTFFVYQVVFVYAHNATSAGRQNGNAFAYS
   IRDIG37126_D6A  SEQIDNO:13  FTQSTELAGPGTFFVYQVVFVYAHNATSAGRQNGNAFAYS
   IRDIG37126_G23E SEQIDNO:18  FTQSTELAGPGTFFVYQVVFVYAHNATSAGRQNGNAFAYS
   IRDIG37126_H13A SEQIDNO:14  FTQSTELAGPGTFFVYQVVFVYAHNATSAGRQNGNAFAYS
   IRDIG37126_R28K SEQIDNO:19  FTQSTELAGPGTFFVYQVVFVYAHNATSAGRQNGNAFAYS
   IRDIG37126_R28M SEQIDNO:20  FTQSTELAGPGTFFVYQVVFVYAHNATSAGRQNGNAFAYS
```

Fig. 6C

```
                                          201                                      240
            IRDIG37126 SEQIDNO:2  KTQQVDSRLDLYYLSAITQDRTVIVESSKAINPLDWDTVQ
       IRDIG37126_D18A SEQIDNO:15  KTQQVDSRLDLYYLSAITQDRTVIVESSKAINPLDWDTVQ
       IRDIG37126_D18S SEQIDNO:17  KTQQVDSRLDLYYLSAITQDRTVIVESSKAINPLDWDTVQ
  IRDIG37126_D18L_D75E SEQIDNO:23  KTQQVDSRLDLYYLSAITQDRTVIVESSKAINPLDWDTVQ
  IRDIG37126_D18Q_D75E SEQIDNO:24  KTQQVDSRLDLYYLSAITQDRTVIVESSKAINPLDWDTVQ
  IRDIG37126_D18R_D75E SEQIDNO:22  KTQQVDSRLDLYYLSAITQDRTVIVESSKAINPLDWDTVQ
       IRDIG37126_D18P SEQIDNO:16  KTQQVDSRLDLYYLSAITQDRTVIVESSKAINPLDWDTVQ
       IRDIG37126_D75A SEQIDNO:21  KTQQVDSRLDLYYLSAITQDRTVIVESSKAINPLDWDTVQ
        IRDIG37126_D6A SEQIDNO:13  KTQQVDSRLDLYYLSAITQDRTVIVESSKAINPLDWDTVQ
       IRDIG37126_G23E SEQIDNO:18  KTQQVDSRLDLYYLSAITQDRTVIVESSKAINPLDWDTVQ
       IRDIG37126_H13A SEQIDNO:14  KTQQVDSRLDLYYLSAITQDRTVIVESSKAINPLDWDTVQ
       IRDIG37126_R28K SEQIDNO:19  KTQQVDSRLDLYYLSAITQDRTVIVESSKAINPLDWDTVQ
       IRDIG37126_R28M SEQIDNO:20  KTQQVDSRLDLYYLSAITQDRTVIVESSKAINPLDWDTVQ 241                          271
            IRDIG37126 SEQIDNO:2  RNVLIENYNPASNSGHFRFDWSAYNDPHRRY
       IRDIG37126_D18A SEQIDNO:15  RNVLIENYNPASNSGHFRFDWSAYNDPHRRY
       IRDIG37126_D18S SEQIDNO:17  RNVLIENYNPASNSGHFRFDWSAYNDPHRRY
  IRDIG37126_D18L_D75E SEQIDNO:23  RNVLIENYNPASNSGHFRFDWSAYNDPHRRY
  IRDIG37126_D18Q_D75E SEQIDNO:24  RNVLIENYNPASNSGHFRFDWSAYNDPHRRY
  IRDIG37126_D18R_D75E SEQIDNO:22  RNVLIENYNPASNSGHFRFDWSAYNDPHRRY
       IRDIG37126_D18P SEQIDNO:16  RNVLIENYNPASNSGHFRFDWSAYNDPHRRY
       IRDIG37126_D75A SEQIDNO:21  RNVLIENYNPASNSGHFRFDWSAYNDPHRRY
        IRDIG37126_D6A SEQIDNO:13  RNVLIENYNPASNSGHFRFDWSAYNDPHRRY
       IRDIG37126_G23E SEQIDNO:18  RNVLIENYNPASNSGHFRFDWSAYNDPHRRY
       IRDIG37126_H13A SEQIDNO:14  RNVLIENYNPASNSGHFRFDWSAYNDPHRRY
       IRDIG37126_R28K SEQIDNO:19  RNVLIENYNPASNSGHFRFDWSAYNDPHRRY
       IRDIG37126_R28M SEQIDNO:20  RNVLIENYNPASNSGHFRFDWSAYNDPHRRY
```

HEMIPTERAN ACTIVE INSECTICIDAL PROTEIN

CROSS REFERENCE TO RELATED APPLICATIONS

This application claims the benefit of U.S. Provisional Patent Application Ser. No. 62/583,684 filed Nov. 9, 2017, which is expressly incorporated by reference in its entirety herein.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 70.2 KB ASCII (Text) file named "81125 Sequences_ST25" created on Oct. 25, 2018.

TECHNICAL FIELD

The present invention relates generally to the field of molecular biology as applied to agricultural sciences. More particularly, certain embodiments concern methods for the use of polynucleotide sequences as templates for protein production, and the use of proteins for insect control. Also disclosed are methods of making and using the polynucleotide sequences in the development of the novel pesticidal proteins in transgenic plant cells containing the polynucleotide sequences disclosed herein.

BACKGROUND

Biological control of insect pests of agricultural significance using a pesticidal protein affords an environmentally friendly and commercially attractive alternative to synthetic chemical pesticides. Generally speaking, the use of pesticidal proteins presents a lower risk of pollution and environmental hazards, and pesticidal proteins provide greater target specificity than is characteristic of traditional broad-spectrum chemical insecticides. In addition, pesticidal proteins often cost less to produce and thus improve economic yield for a wide variety of crops.

Certain species of microorganisms of the genus *Bacillus* are known to possess insecticidal activity against a range of insect pests including Lepidoptera, Diptera, Coleoptera, Hemiptera and others. *Bacillus thuringiensis* and *Bacillus popilliae* are among the most successful pesticidal proteins discovered to date. Insect pathogenicity has also been attributed to strains of *B. larvae, B. lentimorbus, B. sphaericus* and *B. cereus,* Pesticidal proteins, particularly those obtained from *Bacillus* strains, have played an important role in agriculture as alternatives to the use of synthetic chemical pesticides for insect control.

Crop plants have been developed with enhanced insect resistance by genetically engineering crop plants to produce pesticidal proteins from *Bacillus*. For example, coin and cotton plants have been genetically engineered to produce pesticidal proteins isolated from strains of *Bacillus thuringiensis*. These genetically engineered crops containing novel pesticidal proteins are now widely used in agriculture and have provided the farmer with an environmentally friendly alternative to traditional insect control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, for example pesticidal proteins which are active against a variety of insects in the order Lepidoptera and the order Hemiptera including but not limited to species belonging to the family Pentatomidae, the family Plataspidae and the family Cydnidae. In addition, there remains a need for pesticidal proteins having activity against a variety of insect pests that have developed resistance to existing pesticides.

BRIEF SUMMARY

In embodiments of the subject disclosure, the disclosure relates to an isolated nucleic acid molecule comprising a polynucleotide encoding an IRDIG37126 polypeptide or variant thereof. In some aspects of this embodiment, the IRDIG37126 polypeptide or variant thereof is orally active. In other aspects of this embodiment, the IRDIG37126 polypeptide or variant thereof has insecticidal activity against an insect pest in the order Hemiptera. Further aspects include where the IRDIG37126 polypeptide or variant thereof has insecticidal activity against an insect pest in the family Pentatomidae. In an aspect of the embodiment, the IRDIG37126 polypeptide or variant thereof comprises a polypeptide having at least 80%, 82.5%, 85%, 87.5%, 90%, 91%, 92%, 93%, 94%, 95%, 96%, 97%, 98%, 99%, 99.5%, 99.9%, or 100% identity to the amino acid sequence of SEQ ID NO:2 or SEQ ID NO:13-24. In some aspects, the isolated nucleic acid molecule comprises a polynucleotide of SEQ ID NO:1 or SEQ ID NO:25-36, a fragment or a complement thereof. In further aspects, the IRDIG37126 polypeptide or variant thereof comprises an amino acid sequence of SEQ ID NO:2 or SEQ ID NO:13-24 or a fragment thereof. In another aspect, the IRDIG37126 polypeptide of SEQ ID NO:2 or SEQ ID NO:13-24 further comprises at least one amino acid substitution, at least one amino acid addition or at least one amino acid deletion. In a further aspect, the IRDIG37126 polypeptide or variant thereof consists of SEQ ID NO:2 or SEQ ID NO:13-24.

In embodiments of the subject disclosure, the disclosure relates to a plant or progeny thereof, comprising an isolated nucleic acid molecule that encodes an IRDIG37126 polypeptide or variant thereof. In some aspects, the plant or progeny thereof is stably transformed with the isolated nucleic acid molecule that encodes an IRDIG37126 polypeptide or variant thereof. In a further aspect, the plant is a monocotyledon. In another aspect, the plant is a dicotyledon. Examples of the plant comprising an isolated nucleic acid molecule that encodes an IRDIG37126 polypeptide or variant thereof can include *Zea mays*, wheat, rice, sorghum, oats, rye, bananas, sugar cane, *Glycine max*, cotton, *Arabidopsis*, tobacco, sunflower, and canola. In another aspect, the plant comprising an isolated nucleic acid molecule that encodes an IRDIG37126 polypeptide or variant thereof can further comprise one or more additional transgenic traits. Examples of such additional transgenic traits include trait that encode a selectable marker protein, an insecticidal resistance protein, a herbicide tolerance protein, a nitrogen use efficiency protein, a water use efficiency protein, a small RNA molecule, a nutritional quality protein, or a DNA binding protein. In other aspects, the plant produces a commodity product. Examples of such commodity products include protein concentrate, protein isolate, grain, meal, flour, oil, or fiber. In another aspect, the plant comprising an isolated nucleic acid molecule that encodes an IRDIG37126 polypeptide or variant thereof is used to protecting the plant from an insect pest.

In embodiments of the subject disclosure, the disclosure relates to a method for producing a plant cell. The method includes the following steps: a) transforming a plant cell with a gene encoding the IRDIG37126 polypeptide or variant thereof; b) isolating the transformed plant cell comprising the gene encoding the IRDIG37126 polypeptide or variant thereof; and, c) producing a transgenic plant cell comprising the gene encoding the IRDIG37126 polypeptide or variant thereof. The method may include the additional steps of: d) regenerating the transgenic plant cell into a transgenic plant; and, e) obtaining the transgenic plant, wherein the transgenic plant comprises the gene encoding the IRDIG37126 polypeptide or variant thereof. In an additional aspect, the transformation of the plant cell is performed with a plant transformation method. Examples of such transformation methods include *Agrobacterium*-mediated transformation method, a biolistics transformation method, a silicon carbide transformation method, a protoplast transformation method, and a liposome transformation method. In further aspects, the polynucleotide sequence of interest is constitutively expressed in a plant cell. In additional aspects, the polynucleotide sequence of interest is stably integrated into the genome of the transgenic plant cell. In some aspects the transgenic plant cell is a monocotyledonous transgenic plant cell or a dicotyledonous transgenic plant cell. Examples of dicotyledonous transgenic plant cells include an *Arabidopsis* plant cell, a tobacco plant cell, a *Glycine max* plant cell, a canola plant cell, and a cotton plant cell. Examples of monocotyledonous transgenic plant cells include a *Zea mays* plant cell, a rice plant cell, and a wheat plant cell. In another aspect, the plant cell comprising an isolated nucleic acid molecule that encodes an IRDIG37126 polypeptide or variant thereof is used to protecting the plant from an insect pest.

In embodiments of the subject disclosure, the disclosure relates to a method for expressing a polynucleotide sequence of interest in a plant cell, the method comprising introducing into the plant cell a gene expression cassette comprising the gene encoding the IRDIG37126 polypeptide or variant thereof. In some aspects, the gene expression cassette comprising the gene encoding the IRDIG37126 polypeptide or variant thereof is introduced into the plant cell by a plant transformation method. Examples of such a transformation method include an *Agrobacterium*-mediated transformation method, a biolistics transformation method, a silicon carbide transformation method, a protoplast transformation method, and a liposome transformation method. In other aspects, the polynucleotide sequence of interest is expressed constitutively in plant cell tissue. In further aspects, the polynucleotide sequence of interest is stably integrated into the genome of the plant cell. In additional aspects, the transgenic plant cell is a monocotyledonous plant cell or a dicotyledonous plant cell. Examples of dicotyledonous plant cells include an *Arabidopsis* plant cell, a tobacco plant cell, a *Glycine max* plant cell, a canola plant cell, and a cotton plant cell. Examples of monocotyledonous plant cells include a *Zea mays* plant cell, a rice plant cell, and a wheat plant cell. In another aspect, the plant or cell comprising an isolated nucleic acid molecule that encodes an IRDIG37126 polypeptide or variant thereof is expressed in the plant or cell to protecting the plant from an insect pest.

In embodiments of the subject disclosure, the disclosure relates to a gene expression cassette comprising a promoter operably linked to a heterologous coding sequence, wherein the heterologous coding sequences encodes an IRDIG37126 polypeptide or variant thereof. In some aspects, the heterologous coding sequences encoding an IRDIG37126 polypeptide or variant thereof has at least 80%, 82.5%, 85%, 87.5%, 90%, 91%, 92%, 93%, 94%, 95%, 96%, 97%, 98%, 99%, 99.5%, 99.9%, or 100% identity to the amino acid sequence of SEQ ID NO:2 or SEQ ID NO:13-24. In other aspects, the heterologous coding sequences encoding an IRDIG37126 polypeptide or variant thereof consists of the amino acid sequence of SEQ ID NO:2 or SEQ ID NO:13-24. In further aspects, the heterologous coding polynucleotide sequence encoding the IRDIG37126 polypeptide or variant thereof comprises a polynucleotide sequence with at least 80%, 82.5%, 85%, 87.5%, 90%, 91%, 92%, 93%, 94%, 95%, 96%, 97%, 98%, 99%, 99.5%, 99.9%, or 100% identity to the polynucleotide sequence of SEQ ID NO:1 or SEQ ID NO:25-36. In other aspects, the gene expression cassette further comprises one or more additional transgenic traits. Examples of such additional transgenic traits include heterologous coding sequence conferring insecticidal resistance, herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker. In an additional aspect, the heterologous coding sequence is operably linked to one or more regulatory sequences that drive expression of the IRDIG37126 polypeptide or variant thereof. In further aspects, the IRDIG37126 polypeptide or variant thereof is orally active. In other aspects, the IRDIG37126 polypeptide or variant thereof has insecticidal activity against an insect pest of the order Hemiptera. In an aspect, the IRDIG37126 polypeptide or variant thereof has insecticidal activity against an insect pest of the Pentatomidae family. In another aspect, the IRDIG37126 polypeptide or variant thereof has insecticidal activity against an insect pest of the order Lepidoptera such as Soybean Looper. In a further aspect, the recombinant vector comprising the gene expression cassette of is a plasmid, a cosmid, a bacterial artificial chromosome, a virus, and a bacteriophage. In other embodiments, the gene expression cassette is contained within a recombinant microbial cell. Examples of such a recombinant microbial cell includes a bacteria, baculovirus, algae, yeast, and fungi. Further examples of a bacterial cell include a *Pseudomonas* cell, an *Agrobacterium* cell, and *Escherichia* cell. In some aspects, the recombinant microbial cell is cultured under conditions which the heterologous coding sequence encoding the IRDIG37126 polypeptide or variant thereof is expressed to produce a polypeptide with insecticidal activity. In further embodiments, the gene expression cassette is contained within a transgenic cell. In some aspects, the transgenic cell is a transgenic plant cell. In other embodiments, the gene expression cassette is contained within a transgenic plant. In an aspect the transgenic plant is a monocotyledonous plant or dicotyledonous plant. Examples of such a monocotyledonous plant include a maize plant, a rice plant, and a wheat plant. In another embodiment, the gene expression cassette is contained within a plant seed.

In embodiments of the subject disclosure, the disclosure relates to a method for controlling an insect pest population, comprising contacting the insect pest population with an insecticidally-effective amount of a recombinant IRDIG37126 polypeptide or variant thereof. In an aspect, the insect pest is exposed to a transgenic plant cell, plant or plant part, wherein said plant cell, plant or plant part expresses an insecticidally-effective amount of the recombinant IRDIG37126 polypeptide or variant thereof. In further aspects the insect pest is from the Lepidopteran and/or Hemipteran species. In further aspects, the plant is planted within a crop field.

In further embodiments, the subject disclosure relates to a method of inhibiting growth or killing an insect pest, comprising contacting the insect pest with an insecticidally-effective amount of a recombinant IRDIG37126 polypeptide or variant thereof. In an aspect, the insect pest is exposed to a transgenic plant cell, plant or plant part, wherein said plant cell, plant or plant part that expresses an insecticidally-effective amount of the recombinant IRDIG37126 polypeptide or variant thereof. In other aspects, the insect pest is from the Lepidopteran and/or Hemipteran species. In further aspects, the plant is planted within a crop field.

In other embodiments, the subject disclosure relates to a method for controlling an insect pest population resistant to a pesticidal protein, comprising contacting the insect pest population with an insecticidally-effective amount of a recombinant IRDIG37126 polypeptide or variant thereof. Examples of such a pesticidal protein, for which insect pest populations are resistant, include a Cry1Ac protein, a Cry1Ab protein, a Cry1A.105 protein, a Cry1Ac protein, a Cry1 F protein, a Cry1 Fa2 protein, a Cry1 F protein, a Cry2Ab protein, a Cry3A protein, a mCry3A protein, a Cry3Bb1 protein, a Cry34Ab1 protein, a Cry35Ab1 protein, a Vip3A protein, a Cry9c protein, a eCry3.1 Ab protein, a CBI-Bt protein, a patatin protein, a plant lectin protein, a phytoecdysteroid protein, a *Xenorhabdus* insecticidal protein, a *Photorhabdus* insecticidal protein, a *Bacillus laterosporous* insecticidal protein, and a *Bacillus sphaericus* insecticidal protein. In another aspect, the insect pest is exposed to a transgenic plant cell, plant or plant part that expresses an insecticidally-effective amount of the recombinant IRDIG37126 polypeptide or variant thereof. In further aspects, the insect pest is from a Lepidopteran and/or Hemipteran species. In further aspects, the plant is planted within a crop field.

In an additional embodiment, the subject disclosure relates to a method for protecting a plant from an insect pest, comprising expressing in the plant or cell thereof an isolated insecticidal protein of a recombinant IRDIG37126 polypeptide or variant thereof. In another aspect, the insect pest is exposed to a transgenic plant cell, plant or plant part, wherein said plant cell, plant or plant part expresses an insecticidally-effective amount of the recombinant IRDIG37126 polypeptide or variant thereof. In other aspects, the insect pest is from the Lepidopteran and/or Hemipteran species. In further aspects, the plant is planted within a crop field.

In an additional embodiment, the subject disclosure relates to a method of reducing the emergence of Lepidoptera and/or Hemiptera insects that are resistant to transgenic plants. In an aspect the transgenic plants are transformed with a polynucleotide expressing a recombinant IRDIG37126 insecticidal protein. In another aspect the polynucleotide expressing a recombinant IRDIG37126 insecticidal protein is expressed in combination with an insecticidal protein that has a different mode of action as compared to the IRDIG37126 insecticidal protein. In other aspects, the transgenic plant comprising the IRDIG37126 insecticidal protein in combination with the other insecticidal protein has insecticidal activity against an insect pest in the order Hemiptera and/or Lepidoptera. In further aspects, the plant is planted within a crop field.

In a further embodiment, the subject disclosure relates to a method for Lepidoptera and/or Hemiptera insect resistance management. The method comprising the step of co-expressing two or more insecticidal molecules that are toxic to Lepidoptera and/or Hemiptera insects in a transgenic plant. In an aspect the two or more insecticidal molecules exhibit different modes of action of insecticidal activity against the Lepidoptera and/or Hemiptera insects. In further aspects the insecticidal activity is insect growth inhibition. In other aspects the insecticidal activity is insect mortality. In an aspect the two or more insecticidal molecules comprise a recombinant IRDIG37126 insecticidal protein and a Cry protein. additional aspects the two or more insecticidal molecules comprise a recombinant IRDIG37126 insecticidal protein and a VIP protein. In further aspects the two or more insecticidal molecules comprise a recombinant IRDIG37126 insecticidal protein and a small RNA molecule. In further aspects, the transgenic plant is planted within a crop field.

In a further embodiment, the subject disclosure relates to a composition, comprising an insecticidally-effective amount of a recombinant IRDIG37126 polypeptide or variant thereof. In other aspects of this embodiment, the composition further comprises an agriculturally suitable carrier, a surfactant, an organosilicone, a safener, a fertilizer, a micronutrient, an insect attractant, and an insect growth regulator. An example of the carrier can include a powder, a dust, pellets, granules, spray, emulsion, colloid, and solution. In other aspects, the composition further comprises one or more herbicides, insecticides or fungicides. In some aspects the one or more insecticides are pesticidal proteins. Examples of such pesticidal proteins include a Cry1 protein, a Cry2 protein, a Cry3 protein, a Cry4 protein, a Cry5 protein, a Cry6 protein, a Cry7 protein, a Cry8 protein, a Cry9 protein, a Cry15 protein, Cry22 protein, a Cry23 protein, a Cry32 protein, a Cry34 protein, a Cry35 protein, a Cry36 protein, a Cry37 protein, a Cry43 protein, a Cry46 protein, a Cry51 protein, a Cry55 protein, a Cry binary toxin, a Cyt protein, a VIP toxin, a SIP protein, an insecticidal lipase, an insecticidal chitinase, a snake venom protein, a patatin protein, a plant lectin protein, a phytoecdysteroid protein, a *Xenorhabdus* insecticidal protein, a *Photorhabdus* insecticidal protein, a *Bacillus* laterosporous insecticidal protein, and a *Bacillus sphaericus* insecticidal protein. In other aspects, the one or more insecticides are pesticidal chemicals. Examples of such a pesticidal chemical includes pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates.

In a further embodiment, the subject disclosure relates to a recombinant hemipteran-active polypeptide, comprising one or more properties selected from: a) a polypeptide comprising at least 80%, 82.5%, 85%, 87.5%, 90%, 91%, 92%, 93%, 94%, 95%, 96%, 97%, 98%, 99%, 99.5%, 99.9%, or 100% sequence identity to SEQ ID NO:2 or SEQ ID NO:13-24; b) an enzymatically active fragment of SEQ ID NO:2 or SEQ ID NO:13-24; c) a polypeptide variant of a) or b); or, e) a peptide segment exhibiting at least 80%, 82.5%, 85%, 87.5%, 90%, 91%, 92%, 93%, 94%, 95%, 96%, 97%, 98%, 99%, or 100% amino acid sequence identity to SEQ ID NO:2 or SEQ ID NO:13-24. In an aspect the recombinant hemipteran-active polypeptide comprising insecticidal activity. In further aspects the insecticidal activity comprises insecticidal activity against an insect pest of the order Lepidoptera. In other aspects the recombinant hemipteran-active polypeptide has insecticidal activity that comprises orally active insecticidal activity. In other aspects, SEQ ID NO:2 or SEQ ID NO:13-24 further comprises at least one amino acid substitution, at least one amino acid addition or at least one amino acid deletion.

In a further embodiment, the subject disclosure relates to an isolated polynucleotide encoding the recombinant hemipteran-active polypeptide, wherein the isolated polynucleotide is selected from the group consisting of: a) a nucleotide sequence of SEQ ID NO:1 or SEQ ID NO:25-36; b) a nucleotide sequence encoding a polypeptide of SEQ ID NO:2 or SEQ ID NO:13-24; c) a nucleotide sequence that hybridizes with a) under stringent hybridization conditions; d) a complementary strand of a) or b); e) a fragment of a) or b) comprising at least 20 nucleotides; and f) a nucleotide sequence that is degenerate as a result of the genetic code to any one of the sequences as defined in a) or b).

In some embodiments the disclosure relates to a polynucleotide operably linked to a heterologous promoter, wherein the polynucleotide encodes a polypeptide having at least 90%, 91%, 92%, 93%, 94%, 95%, 96%, 97%, 98%, or 99% sequence identity with the amino acid sequence of SEQ ID NO:2 or SEQ ID NO:13-24, that when aligned with SEQ ID NO:2 or SEQ ID NO:13-24, comprises an glutamine at the position corresponding to position 19 of SEQ ID NO:2 or SEQ ID NO:13-24,a leucine at the position corresponding to position 20 of SEQ ID NO:2 or SEQ ID NO:13-24, a histidine at the position corresponding to position 21 of SEQ ID NO:2 or SEQ ID NO:13-24, a valine at the position corresponding to position 22 of SEQ ID NO:2 or SEQ ID NO:13-24, a glycine at the position corresponding to position 23 of SEQ ID NO:2 or SEQ ID NO:13-24, a glutamic acid at the position corresponding to position 24 of SEQ ID NO:2 or SEQ ID NO:13-24, and a valine at the position corresponding to position 25 of SEQ ID NO:2 or SEQ ID NO:13-24. In some embodiments the IRDIG37126 polypeptide variant comprising any one or more amino acid substitutions corresponding to positions 6, 13, 18, 23, 28, or 75 of SEQ ID NO:2 or SEQ ID NO:13-24, in any combination. In some embodiments the disclosure relates to a method for controlling, inhibiting growth, or killing an insect pest population, comprising a step of administering a polynucleotide such that the polynucleotide contacts the insect pest, wherein the peptide comprises the amino acid sequence QLHVGEV (SEQ ID NO:37) or a variant of SEQ ID NO:37, said variant having at least 90%, 91%, 92%, 93%, 94%, 95%, 96%, 97%, 98%, or 99% sequence identity to SEQ ID NO:37. In other embodiments the disclosure relates to a polynucleotide that has insecticidal activity and has an amino acid sequence including, when aligned with an amino acid sequence consisting of SEQ ID NO:2, the following motif of QLHVGEV (SEQ ID NO:37). In further embodiments the disclosure relates to a transgenic plant cell comprising a recombinant polynucleotide that encodes an IRDIG37126 protein that exhibits insecticidal activity wherein said activity inhibits growth of an insect pest, further wherein said IRDIG37126 protein comprises an amino acid sequence having at least 97.8% sequence identity with SEQ ID NO:2; and an IRDIG37126 motif having the general formula of QLHVGEV (SEQ ID NO:37).

The foregoing and other features will become more apparent from the following detailed description of several embodiments, which proceeds with reference to the accompanying figures.

BRIEF DESCRIPTION OF THE FIGURES

FIG. 1 provides a sequence alignment of the IRDIG37126 protein of SEQ ID NO:2 with the PIP-1 of SEQ ID NO:3 (polynucleotide sequence listing number 2 of U.S. Pat. No. 9,688,730) and IRDIG22274 of SEQ ID NO:4 (Genbank Acc. No. WP_011534324) proteins.

FIG. 4 provides a graph of the evaluation of the expressed IRDIG37126 protein in the standard diet based bioassay at various doses. The Y-axis shows percent mortality average of 3 replicate wells. The samples tested include; Diet only (negative control), Positive (IRDIG31502 at 1000 ppm), S1-2000 ppm (IRDIG37126 tested at 2000 ppm final concentration), S2-1500 ppm (IRDIG37126 tested at 1500 ppm), S3-1000 ppm (IRDIG37126 tested at 1000 ppm), S4-500 ppm (IRDIG37126 tested at 500 ppm), S5-250 ppm (IRDIG37126 tested at 250 ppm), and S6-125 (IRDIG37126 tested at 125 ppm).

FIG. 5 provides a graph of the evaluation of the IRDIG37126 protein in the standard diet based bioassay at various doses. The Y-axis shows percent mortality. Each point represents the percent of insect mortality in a single well. The IRDIG37126 protein of the subject disclosure showed higher mortality rates at lower doses as compared to the control insecticidal IRDIG31502 protein.

FIGS. 6A, 6B, and 6C provide a sequence alignment of the IRDIG37126 protein of SEQ ID NO:2 with the variant IRDIG37126 proteins of SEQ ID NO:13-24. The alignments were made using the AlignX alignment program of the Vector NTI suite (Invitrogen, Carlsbad, Calif.). The proteins share at least 97.8% sequence identity with one another as a result of the various mutations that were produced throughout the protein sequence.

SEQUENCE LISTING

The nucleic acid sequences listed in the accompanying sequence listing are shown using standard letter abbreviations for nucleotide bases, as defined in 37 C.F.R. § 1.822. In view of the redundancy of the genetic code, it will be understood that a nucleotide sequence including a coding sequence also describes the genus of polynucleotides encoding the same polypeptide as a polynucleotide consisting of the reference sequence. Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence,

DETAILED DESCRIPTION

I. Overview of Several Embodiments

Figure 2:
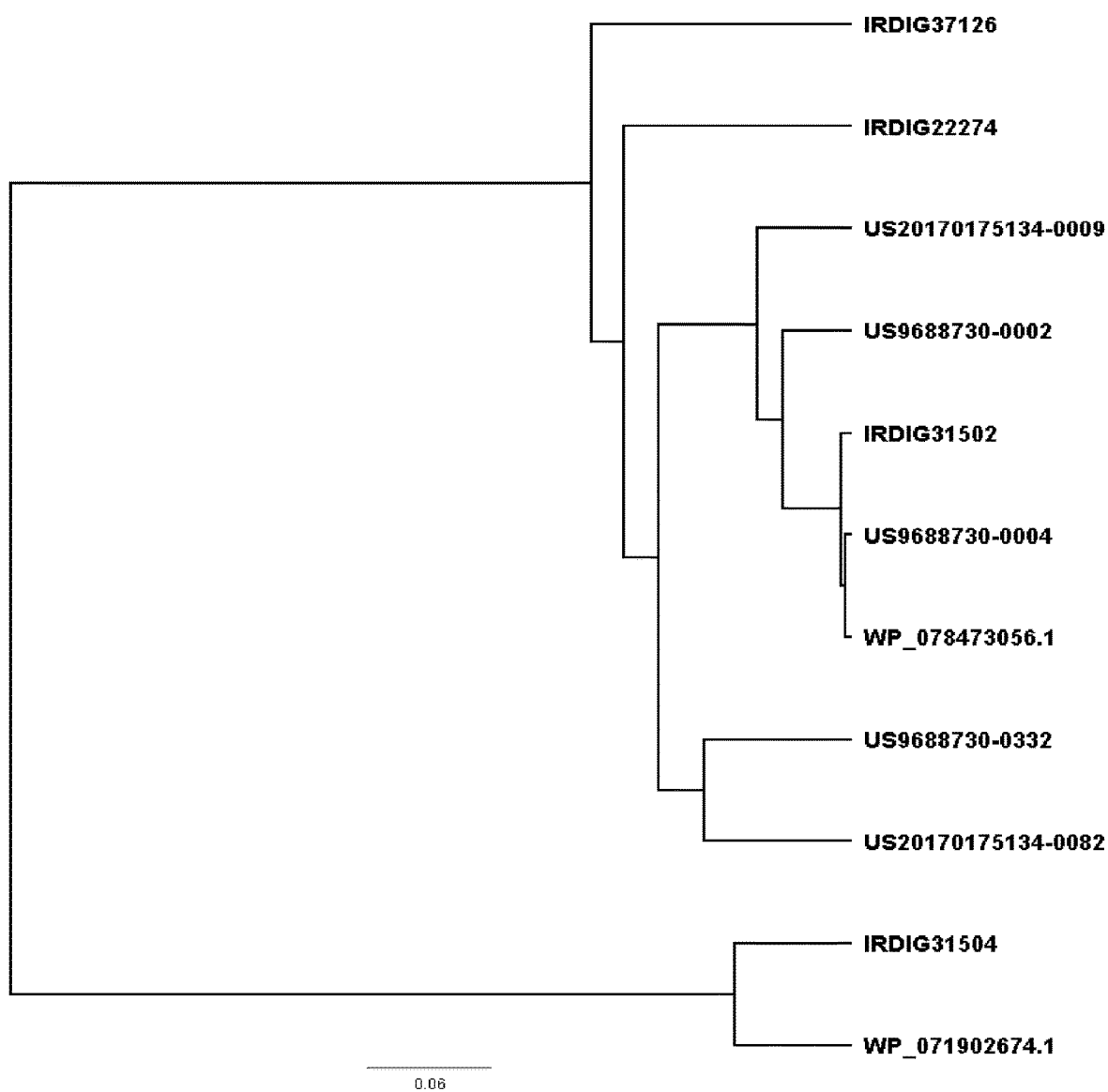
FIG. 2. provides a phylogenetic tree alignment of the IRDIG37126 protein of SEQ ID NO:2 with the proteins listed in Table 1. The phylogenetic tree includes IRDIG31504 (Genbank Acc. No. EPX60094.1, provided herein as SEQ ID NO:11) and WP_071902674.1 (Genbank Acc. No. WP_071902674.1, provided herein as SEQ ID NO:12) these two proteins that do not have activity against Hemipteran insects like BSB.

The identification of novel pesticidal proteins that can control insect species are beneficial for modern crop production systems. The present disclosure provides compositions and methodologies for controlling such insect pests. For the first time, novel pesticidal proteins that confer insecticidal activity against such insect pests are provided. In addition, the polynucleotides encoding such pesticidal proteins that confer insecticidal activity against the insect pests are provided. These biological molecules can be engineered into gene expression cassettes and transformed into plants, plant cells, plant seeds, or plant parts to provide resistance against insect pests. Or, the biological molecules of the subject disclosure can be engineered into gene expression cassettes that are transformed into microorgansims such as bacteria, viruses, yeast, or fungi. The resulting compositions that contain the novel insecticidal activity can be used to control an insect pest population or to reduce the emergence of insect resistance within transgenic plants. These compositions and methodologies provided in the subject disclosure serve to control such insect pests.

Insect pests of the Order Hemipteran—such as stink bugs—cause significant economical problems in crop plants by feeding on the crop plants. This behavior results in damage and destruction of the crop plants. Moreover, these insect pests infest crop plants throughout the world, especially in Latin America. These pests may feed on soybean, tobacco, peaches, crucifers, tomatoes, small grains, red clover, and cotton. In addition, they may feed on corn in specific instances. Stink bugs typically feed on plant fluids by inserting their needlelike mouthparts into stems, leaves or seed pods. While feeding, they inject materials into the plant to aid in digestion and sap removal. Penetration by the mouthparts can cause physical damage, much like stabbing the plant with a fine needle. A combination of mechanical and chemical damage to the growing point of the plant may be responsible for the injury and symptoms seen in the crop field. Typically, stink bug feeding causes three types of damage. They may kill small seedlings, produce stunted plants, or cause "suckering" (the production of tillers from the base of damaged plants). Frequently a series of plants along a row may exhibit a progression of these symptoms, giving a stair step appearance (dead seedlings, stunted plants, and tillering). To date only a few proteins from the monalysin superfamily of *Pseudomonas* toxins have been identified and exemplified to control insect pests of the Hemipteran Order, such as stink bugs.

Nevertheless, the IRDIG37126 polypeptide of the subject disclosure provide a novel monalysin family member that shares ~80% sequence identity at the amino acid level to other publically known monalysin insect resistant proteins. For instance, the IRDIG37126 polypeptide was compared to other known monalysin protein sequences. IRDIG37126 was found to have 79.7% identity to PIP-1 (polynucleotide sequence listing number 2 of U.S. Pat. No. 9,688,730) and 74.2% identity to the prototypical monalysin of IRDIG22274 (Genbank Acc. No. WP_011534324,); both molecules have been identified as having insecticidal activity against Hemipteran species like the sting bug. In addition, IRDIG37126 was found to have 80.1% identity with the protein of Genbank Acc. No. WP_078473056.1; IRDIG37126 was found to have 80.8% identity with the protein of Genbank Acc. No. WP_020294695.1; IRDIG37126 was found to have 80.6% identity with the protein of polynucleotide sequence listing number 4 of U.S. Pat. No. 9,688,730; IRDIG37126 was found to have 79.9% identity with the protein of polynucleotide sequence listing number 9 of U.S. Patent App. No. 20170175134; IRDIG37126 was found to have 76.0% identity with the protein of polynucleotide sequence listing number 332 of U.S. Pat. No. 9,688,730; and IRDIG37126 was found to have 77.1% identity with the protein of polynucleotide sequence listing number 82 of U.S. Patent App. No. 20170175134. From this bioinformatical analysis, it was determined that the novel protein sequence of IRDIG37126 shared at most 80.8% sequence identity with a known monalysin protein sequence.

The present disclosure is drawn to compositions and methods for controlling insect pests through the use the IRDIG37126 polypeptide or variant thereof, or polynucleotide sequences encoding this polypeptide. In particular, the nucleic acid sequences of the embodiments are useful for preparing plants, compositions and microorganisms that possess insecticidal activity as conferred by the IRDIG37126 polypeptide or variant thereof. For instance the IRDIG37126 polypeptide or variant thereof results in significant growth inhibition and mortality of insect pests. Moreover, the IRDIG37126 polypeptide or variant thereof and polynucleotide sequences that encode this polypeptide can be used to identify and isolate other variant (e.g., homologous or partially homologous) sequences that contain insecticidal activity, and for the generation of altered IRDIG37126 polypeptide or variant thereof sequences by methods known in the art, such as site directed mutagenesis, domain swapping or DNA shuffling. The IRDIG37126 polypeptide and variant sequences can be used for controlling, inhibiting growth or killing insect pests; such as stink bugs and Soybean Looper.

II. Terms and Abbreviations

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence has been introduced into a host cell by genetic engineering (or the progeny thereof) where the transgene/heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

As used herein, "heterologous DNA coding sequence" means any coding sequence other than the one that naturally encodes the IRDIG37126 protein, or any homolog/variant of the expressed IRDIG37126 protein. The term "heterologous" is used in the context of this disclosure for any combination of nucleic acid sequences that is not normally found intimately associated in nature.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual*, 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions: Very High Stringency: Hybridization in 5×SSC buffer at 65° C. for 16 hours; was twice in 2×SSC buffer at room temperature for 15 minutes each; and wash twice in 0.5×SSC buffer at 65° C. for 20 minutes each. High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each. Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query") polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present disclosure is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the disclosure, function of a query polypeptide is inferred from function of a conserved protein sequence where either (1) hit_p<1e-30 or % identity >35% AND query_coverage >50% AND hit_coverage >50%, or (2) hit_p<1e-8 AND query_coverage >70% AND hit_coverage >70%.

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, Calif.). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ (©1993-2016). DNASTAR. Madison, Wis.). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. Dec. 15; 73(1):237-44; Higgins and Sharp (1989) CABIOS 5:151-3; Higgins et al. (1992) Comput. Appl. Biosci. 8:189-91). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) J. Mol. Biol. 215:403-10). Further examples of such BLAST alignment programs include Gapped-BLAST or PSI-BLAST (Altschul et al., 1997). In an embodiment, the subject disclosure relates to calculating percent identity between two polynucleotides or amino acid sequences using the EMBOSS suite of alignment programs, including, but not limited to: Matcher, Needle, Stretcher, Water, Wordmatch, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics*, 2:482-489, 1981, Smith et al., *Nucleic Acids Research* 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the disclosure will have at least about 40%, 45%, 50%>, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a nucleotide sequence of the disclosure may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "orally active" refers to a protein that inhibits the proliferation of insect pests when orally ingested by the insect pest.

As used herein, the term "insecticidal activity" refers to activity of an organism or a substance (such as, for example, a protein) that can be measured by, but is not limited to, insect mortality, insect weight loss, insect repellency, and other behavioral and physical changes of an insect after feeding and exposure for an appropriate length of time. Thus, an organism or substance having insecticidal activity adversely impacts at least one measurable parameter of insect fitness.

As used herein, the term "pest" refers to any insect that is unwanted and disruptive or destructive to the growth and development of agricultural crops. The term "insect pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Thysanoptera, Dermaptera, Isoptera, Anoplura, Siphonaptera, Trichoptera, etc., particularly Lepidoptera, and Hemiptera.

As used herein, the term "stable transformation" or "stably transformed" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

As used herein, the term "regeneration" means the process of growing a plant from a plant cell (e.g., plant protoplast or explant).

As used herein, the term "culturing" refers to the in vitro propagation of cells or organisms on or in media of various kinds so that the maintenance or growth cell within a liquid culture medium are controlled under a set of physical conditions. It is understood that the descendants of a cell grown in culture may not be completely identical (i.e., morphologically, genetically, or phenotypically) to the parent cell.

As used herein, the term "controlling" (for instance as in "controlling an insect pest population"), as used herein refers to monitoring, treating, minimizing, exterminating, or preventing insect pests such as stink bugs. In specific instances the insect species are controlled to reducing the number of insects that cause reduced beneficial plant yield.

As used herein, the term "insecticidally-effective amount" refers to a quantity of a substance or organism that has insecticidal activity when present in the environment of an insect pest. For each substance or organism, the insecticidally-effective amount is determined empirically for each pest affected in a specific environment. Similarly, an "pesticidally effective amount" may be used to refer to a insecticidally-effective amount.

As used herein, the term "pesticidal protein" or "insecticidal protein" is intended to refer to a polypeptide that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin, (2011) *PLoS Pathogens*, 7:1-13), from *Pseudomonas protegens* strain CHA0 and Pf-5 (previously *fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcligenes* (Zhang, et al., (2009) Annals of Microbiology 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied* and *Envir. Micro.* 67:2062-2069), U.S. Pat. Nos. 6,048,838, and 6,379,946; and δ-endotoxins. Examples of δ-endotoxins or Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1 Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_CrickmoreSt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

As used herein, the term "inhibiting growth" or "growth inhibition" means a reduction or inhibition in the growth of an insect organism, in some embodiments by at least 10%, 15%, 20%, 25%, 30%, 40%, 45%, 50%, 55%, 60%, 65%, 70%, 75%, 80%, 85%, 90% or 95%. The inhibition of growth of insect can be determined by measuring the weight or size of the insect.

As used herein, the term "mortality" refers to the death of the insects.

As used herein, the term "resistant", "resistance" and "host plant resistance" refers the ability of a host plant to prevent or reduce infestation and damage of a pest from the group comprising insects, nematodes, pathogens, fungi, viruses, and diseases.

As used herein, the term "insect resistance transgene product", can mean a "pesticide", a "Bt" or "Bt polypeptide" where the plant protectant is a protein, or a variant thereof, derived from *Bacillus thuringiensis*, a "non-Bt" or "non-Bt polypeptide", where the plant protectant is a protein, or a variant thereof, derived from a bacterium other than *Bacillus thuringiensis* or a plant, particularly from a fern or other primitive plant, or "RNA" where the plant protectant is an RNA molecule, particularly a RNAi or dsRNA. Transgenic insecticidal products can be expressed from a transgenic event that comprises a transgene encoding the transgenic insect resistance trait.

As used herein, the term "protecting" refers to the avoidance of, or minimizing the amount of attack of plant by a soil pest to a point where it no longer poses a threat to plant vitality, selective plant death, quality loss and/or reduced yields.

As used herein, the term "crop field" refers to a cultivated expanse of land that a farmer uses to grow a crop species. A crop field ranges in size depending on crop species and purpose. In one example, a crop field can include rows and can be planted at various lengths. In another example, a crop field can be planted by broadcasting the seed throughout the crop field. In a further example, a crop field can be planted by drilling the seed throughout the crop field.

As used herein, the term "modes of action" means the biological or biochemical means by which a pest control strategy or compound inhibits pest feeding and/or increases pest mortality.

As used herein, the term "co-expressing" refers to two or more gene products which are produced at the same time within the same host organism.

As used herein, the term "degenerate" refers to a primer or probe nucleic acid in which certain positions are not defined by a single, specific nucleotide. Thus, in such a degenerate position, the primer or probe sequence can be either one of at least two different nucleotides. Such positions often represent difference in genotypes of the target nucleic acid. A degenerate sequence may also be represented as a mixture of multiple non-degenerate individual sequences which, for the purpose of this disclosure, differ in at least two positions.

As used herein, the term "enzymatically active fragment", "fragment" or "biologically active portion" include polypeptide fragments comprising amino acid sequences sufficiently identical to a polypeptide and that exhibit insecticidal activity. "Fragments" or "biologically active portions" include polypeptide fragments comprising amino acid sequences sufficiently identical to the amino acid sequence that exhibit insecticidal activity. A biologically active portion of a polypeptide can be a polypeptide that is, for example, 8, 10, 25, 50, 100, 150, 200, 250 or more amino acids in length. Such biologically active portions can be prepared by recombinant techniques and evaluated for insecticidal activity. As used here, a fragment comprises at least 8 contiguous amino acids of a polypeptide. The embodiments encompass other fragments, however, such as any fragment in the protein greater than about 10, 20, 30, 50, 100, 150, 200, 250 or more amino acids.

As used herein, the term "peptide segment" refers to a protein molecule that has been isolated free of other protein sequences and amino acid residues.

As used herein, the term "DNA segment" refers to a DNA molecule that has been isolated free of total genomic DNA of a particular species. Therefore, a DNA segment encoding a protein or peptide refers to a DNA segment that contains protein coding sequences yet is isolated away from, or purified free from, total genomic DNA of the species from which the DNA segment is obtained, which in the instant case is the genome of the Gram-positive bacterial genus, *Bacillus*, and in particular, the species known as *B. thuringiensis*. Included within the term "DNA segment", are DNA segments and smaller fragments of such segments, and also recombinant vectors, including, for example, plasmids, cosmids, phagemids, phage, viruses, and the like.

As used herein, the term "formulated insecticidal protein" refers to a purified or isolated insecticidal protein that has been expressed or placed into a synthetic composition suitable for agricultural application, including but not limited to transgenic plants, sprayable liquid formulations, powdered solid formulations, or granular formulations.

As used herein, the term "expression" refers to the combination of intracellular processes, including transcription and translation undergone by a coding DNA molecule such as a structural gene to produce a polypeptide.

As used herein, the term "transgenic cell" means any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

As used herein, the term "transgenic plant" means a plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5' UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) Genes & Dev., 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "transcription terminator" or "terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present disclosure. An exemplary sequence includes AAUAAA and variants thereof, as described in Loke J., et al., (2005) Plant Physiology 138(3); 1457-1468.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene/heterologous coding sequence is a gene sequence (e.g., an herbicide-resistance gene), a gene encoding an industrially or pharmaceutically useful compound, or a gene encoding a desirable agricultural trait. In yet another example, the transgene/heterologous coding sequence is an antisense nucleic acid sequence, wherein expression of the antisense nucleic acid sequence inhibits expression of a target nucleic acid sequence. A transgene/heterologous coding sequence may contain regulatory sequences operably linked to the transgene/heterologous coding sequence (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene/heterologous coding sequence of interest, regeneration of a population of plants resulting from the insertion of the transgene/heterologous coding sequence into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene/heterologous coding sequence DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene/heterologous coding sequence of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is typically a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HinduI, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present disclosure is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

III. IRDIG37126 Polypeptide and Nucleic Acids Comprising the Same

Provided are methods and compositions disclosing the IRDIG37126 polypeptide or variant thereof. In an embodiment the IRDIG37126 polypeptide may be SEQ ID NO:2 or SEQ ID NO:13-24. In other embodiments the IRDIG37126 polypeptide may comprise a polypeptide with 80%, 82.5%, 85%, 87.5%, 90%, 91%, 92%, 93%, 94%, 95%, 96%, 97%, 98%, 99%, 99.5% or 100% sequence identity with SEQ ID NO:2 or SEQ ID NO:13-24. In further embodiment the IRDIG37126 polypeptide may comprise SEQ ID NO:2 or SEQ ID NO:13-24. In additional embodiments the IRDIG37126 polypeptide may consist of SEQ ID NO:2 or SEQ ID NO:13-24. Other embodiments include compositions of matter that would allow one with skill in the art to obtain and work with the IRDIG37126 polypeptide or variant thereof. For instance, the IRDIG37126 polypeptide or variant thereof may be provided as an isolated polypeptide sequence. In some aspects the isolated polypeptide sequence may make up a composition. In other instances the IRDIG37126 polypeptide or variant thereof may be provided as a polypeptide expressed in a plant, plant cell, plant seed, or plant part. In additional instances the IRDIG37126 polypeptide or variant thereof may be provided as a polypeptide expressed in a microbial organism.

Further provided are methods and compositions for the use of a polynucleotide sequence encoding an IRDIG37126 polypeptide or variant thereof. In some embodiments the polynucleotide sequence encoding an IRDIG37126 polypeptide comprises SEQ ID NO:1 or SEQ ID NO:25-36. In other embodiments the polynucleotide sequence encoding an IRDIG37126 polypeptide comprises a polynucleotide that shares at least 80%, 82.5%, 85%, 87.5%, 90%, 91%, 92%, 93%, 94%, 95%, 96%, 97%, 98%, 99%, 99.5% or 100% sequence identity with SEQ ID NO:1 or SEQ ID NO:25-36. In further embodiments the polynucleotide sequence encoding an IRDIG37126 polypeptide consists of SEQ ID NO:1 or SEQ ID NO:25-36. Other embodiments include compositions of matter that would allow one with skill in the art to obtain and work with the polynucleotide encoding the IRDIG37126 polypeptide or variant thereof. For instance the polynucleotide encoding the IRDIG37126 polypeptide or variant thereof may be provided in a gene expression cassette. In other instances the polynucleotide encoding the IRDIG37126 polypeptide or variant thereof may be provided in a vector. In additional instances the polynucleotide encoding the IRDIG37126 polypeptide or variant thereof may be provided by integration of the polynucleotide sequence within the genome of a plant, plant cell, plant seed, or plant part. In further instances the polynucleotide encoding the IRDIG37126 polypeptide or variant thereof may be provided as an isolated polynucleotide. In some instances the polynucleotide encoding the IRDIG37126 polypeptide or variant thereof may be provided within a microorganism.

Another aspect of the subject disclosure comprises a functional variant which differs in one or more nucleotides from those of the polynucleotide encoding the IRDIG37126 polypeptide, provided herein. Such a variant is produced as the result of one or more modifications (e.g., deletion, substitution, or addition) of the nucleotide sequences comprising the sequence encoding the IRDIG37126 polypeptide as described herein. In some embodiments, the IRDIG37126 polypeptide is altered to produce a variant IRDIG37126 polypeptide sequence. In an aspect of this embodiment, the variant IRDIG37126 polypeptide shares at least 80%, 82.5%, 85%, 87.5%, 90%, 91%, 92%, 93%, 94%, 95%, 96%, 97%, 98%, 99%, 99.5% or 100% sequence identity with SEQ ID NO:2 or variant thereof. In other aspects the variant IRDIG37126 polypeptide comprises at least one amino acide residue deletion. In further aspects the variant IRDIG37126 polypeptide or variant thereof comprises at least one amino acid residue addition. In some aspects the variant IRDIG37126 polypeptide or variant thereof comprises at least one amino acid residue substitution. In additional aspects the variant IRDIG37126 polypeptide or variant thereof comprises any combination of at least one amino acide residue addition, deletion and/or substitution.

In some embodiments the amino acid and nucleic acid sequences of the subject disclosure may include additional residues, such as additional N- or C-terminal amino acids or 5' or 3' sequences, and yet still be essentially as set forth in one of the sequences disclosed herein, so long as the sequence meets the criteria of maintaining biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The polynucleotide sequences of the present disclosure, regardless of the length of the coding sequence itself, may be combined with other DNA sequences, such as promoters, polyadenylation signals, additional restriction enzyme sites, multiple cloning sites, other coding regions, and the like, such that their overall length may vary considerably. It is therefore contemplated that a polynucleotide sequence of almost any length may be employed, with the total length preferably being limited by the ease of preparation and use in the intended recombinant DNA protocol. For example, polynucleotide sequence fragments may be prepared that include a short contiguous stretch of polynucleotides encoding the whole or a portion of the polypeptide sequence disclosed in SEQ ID NO:2 or SEQ ID NO:13-24, or that are identical to or complementary to DNA sequences which encode the polypeptide sequence disclosed in SEQ ID NO:2 or SEQ ID NO:13-24, and particularly the polynucleotide sequence segment disclosed in SEQ ID NO:1 or SEQ ID NO:25-36.

Recombinant vectors and isolated DNA segments may therefore variously include the peptide-coding regions themselves, coding regions bearing selected alterations or modifications in the basic coding region, or they may encode larger polypeptides that include these polypeptide-coding regions or may encode biologically functional equivalent proteins or polypeptides that have variant amino acids sequences.

The polynucleotide sequences of the present disclosure encompass biologically-functional, equivalent proteins. Such sequences may arise as a consequence of codon redundancy and functional equivalency that are known to occur naturally within polynucleotide sequences and the proteins thus encoded. Alternatively, functionally-equivalent proteins or polypeptides may be created via the application of recombinant DNA technology, in which changes in the protein structure may be engineered, based on considerations of the properties of the amino acids being exchanged. Changes designed by the hand of man may be introduced through the application of site-directed mutagenesis techniques, e.g., to introduce improvements to the antigenicity of the protein or to test mutants in order to examine activity at the molecular level.

In one embodiment, fragments and variants of the polynucleotide encoding the IRDIG37126 polypeptide of SEQ ID NO:2 or SEQ ID NO:13-24 may be used in a DNA construct or in a gene expression cassette to drive expression of a heterologous coding sequence. As described above a fragment refers to a portion of the nucleic acid sequence. Fragments of the polynucleotide encoding the IRDIG37126 polypeptide of SEQ ID NO:2 or SEQ ID NO:13-24 may retain the biological activity of initiating transcription, more particularly driving transcription within plant tissues. Alternatively, fragments of a nucleotide sequence which are useful as hybridization probes may not necessarily retain biological activity. Fragments of a polynucleotide of SEQ ID NO:1 may range from at least about 20 nucleotides, about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, up to the full-length nucleotide sequence of the subject disclosure for the polynucleotide encoding the IRDIG37126 polypeptide of SEQ ID NO:2.

A biologically active portion of the polynucleotide encoding the IRDIG37126 polypeptide of SEQ ID NO:2 can be prepared by isolating a portion of SEQ ID NO:1, and assessing the enzymatic activity of the portion. Nucleic acid molecules that are fragments of a polynucleotide encoding the IRDIG37126 polypeptide of SEQ ID NO:2 comprise at least about 16, 50, 75, 100, 150, 200, 250, 300, 350, 400, 450, 500, 550, 600, 650, 700, 800, or up to the number of nucleotides present in a full-length sequence of SEQ ID NO:1 disclosed herein.

Variant nucleotide sequences also encompass sequences derived from a mutagenic and recombinogenic procedure such as DNA shuffling. With such a procedure, the polynucleotide encoding the IRDIG37126 polypeptide of SEQ ID NO:2 can be manipulated to create a new polynucleotide encoding the IRDIG37126 polypeptide. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA i: 10747-10751; Stemmer (1994) Nature 570:389-391; Crameri et al. (1997) Nature Biotech. 75:436-438; Moore et al. (1997) J. Mol. Biol. 272:336-347; Zhang et al. (1997) Proc. Natl. Acad. Sci. USA 4:4504-4509; Crameri et al. (1998) Nature 527:288-291; and U.S. Pat. Nos. 5,605,793 and 5,837,458.

The nucleotide sequences of the subject disclosure can be used to isolate corresponding sequences from other organisms, particularly other bacterial species such as *Pseudomonas* spp. In this manner, methods such as PCR, hybridization, and the like can be used to identify such sequences based on their sequence identity to the sequences set forth herein. Sequences isolated based on their sequence identity to the entire polynucleotide sequence encoding the IRDIG37126 polypeptide set forth herein or to fragments thereof are encompassed by the present disclosure.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.), hereinafter Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $P^{32}$ or any other detectable marker. Thus, for example, probes for hybridization can be made by labeling synthetic oligonucleotides based on the sequence of the polynucleotide encoding the IRDIG37126 polypeptide or variant thereof of the disclosure. Methods for preparation of probes for hybridization and for construction of genomic libraries are generally known in the art and are disclosed in Sambrook. For example, the entire sequence of the polynucleotide encoding the IRDIG37126 polypeptide or variant thereof is disclosed herein, or one or more portions thereof, may be used as a probe capable of specifically hybridizing to corresponding sequences of the polynucleotide encoding the IRDIG37126 polypeptide or variant thereof and messenger RNAs. To achieve specific hybridization under a variety of conditions, such probes include sequences that are unique among sequences of the polynucleotide encoding the IRDIG37126 polypeptide or variant thereof and are at least about 10 nucleotides in length or at least about 20 nucleotides in length. Such probes may be used to amplify corresponding sequence of the polynucleotide encoding the IRDIG37126 polypeptide or variant thereof from any biological material by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook).

Modifications and changes may be made in the primary structure of the polypeptide sequences of the subject disclosure to produce derivatives, analogs and mutants and DNA segments which encode them and still obtain functional insecticidal activity. In particular embodiments of the disclosure, mutated proteins are contemplated to be useful for increasing the insecticidal activity of the protein, and consequently increasing the insecticidal activity or expression of the recombinant transgene in a plant cell.

For example, certain amino acid residues may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is used in some applications, those which are within ±1 is used in other applications, and those within ±0.5 is used in further applications.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 are applicable in making such modifications, those which are within ±1 are applicable in making such modifications, and those within ±0.5 are applicable in making such modifications.

As outlined above, amino acid substitutions are generally therefore based on the relative similarity of the amino acid side-chain substituents, for example, their hydrophobicity, hydrophilicity, charge, size, and the like. Exemplary substitutions which utilize the foregoing characteristics into consideration are well known to those of skill in the art and include: arginine and lysine; glutamate and aspartate; serine and threonine; glutamine and asparagine; and valine, leucine and isoleucine.

In further embodiments the amino acid substitutions can include modifying the polypeptide of the subject disclosure by making at least one amino acid substitution. In other embodiments the amino acid substitutions can include modifying the polypeptide of the subject disclosure by making at least one amino acid addition. In some embodiments the amino acid substitutions can include modifying the polypeptide of the subject disclosure by making at least one amino acid deletion.

In other embodiments the polypeptides of the subject disclosure can include amino acid sequences deduced from the full-length nucleic acid sequences disclosed herein, and amino acid sequences that are shorter than the full-length sequences, either due to the use of an alternate downstream start site or due to processing that produces a shorter protein having insecticidal activity. Processing may occur in the organism after the protein is expressed in or in the pest after ingestion of the protein.

In some embodiments the amino acid and nucleic acid sequences of the subject disclosure may contain in operable position within the polypeptide a motif peptide segment of SEQ ID NO:37. Wherein the motif peptide segment exhibits at least about 80%, 82.5%, 85%, 87.5%, 90%, 91%, 92%, 93% 94%, 95%, 96%, 97%, 98%, 99%, 99.5%, or 99.9% identity to a consensus sequence specified for the motif peptide segment of SEQ ID NO:37. The motif peptide segment of SEQ ID NO:37 corresponds to amino acid sequence positions 19 through 25 of SEQ ID NO:2, SEQ ID NO:13, SEQ ID NO:14, SEQ ID NO:15, SEQ ID NO: 16, SEQ ID 1\ O:17, SEQ ID NO: 18, SEQ ID NO:19, SFQ ID NO:20, SEQ ID NO:21, SEQ ID NO:22, SEQ ID NO:23, and SEQ ID NO:24. The presence of the motif peptide segment of SEQ ID NO:37 or of a peptide segment exhibiting at least about 80%, 82.5%, 85%, 87.5%, 90%, 91%, 92%, 93%, 94%, 95%, 96%, 97%, 98%, 99%, 99.5%, or 99.9% amino acid sequence identity to this motif peptide segment in a particular toxin protein. is determinative that the toxin protein is a member of the genus of proteins described herein, particularly when the protein is also shown to exhibit insect insecticidal activity properties. Such a motif peptide segment exhibits insecticidal activity against Lepidopteran and/or Hemipteran species.

Another aspect of the subject disclosure includes a nucleic acid vector that comprises a polynucleotide encoding the IRDIG37126 polypeptide or variant thereof as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Recombinant vectors containing the polynucleotide that endcodes the IRDIG37126 polypeptide or variant thereof can be further engineered to contain regulatory elements such as promoters, 5'UTR's, introns, 3' UTR's and terminators. In some embodiments the sequences that make up these regulatory elements may be operably linked to the polynucleotide that endcodes the IRDIG37126 polypeptide or variant thereof. In an embodiment, the polynucleotide that endcodes the IRDIG37126 polypeptide or variant thereof is provided as a gene expression cassette. In preparing the gene expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

In some aspects of this embodiment, the polynucleotide that endcodes the IRDIG37126 polypeptide or variant thereof is positioned under the control of a promoter. In such embodiments, it is contemplated that certain advantages will be gained by positioning the polynucleotide that endcodes the IRDIG37126 polypeptide or variant thereof under the control of a recombinant, or heterologous, promoter. As used herein, a recombinant or heterologous promoter is intended to refer to a promoter that is not normally associated with a DNA segment encoding a protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, inducible, or tissue preferred, and can be used under the appropriate conditions to direct high level expression of the introduced DNA segment within the gene expression cassette, such as is advantageous in the production of recombinant proteins within transgenic plants or in the heterologous expression of recombinant proteins within a microorgansim.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4:645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant—Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In 2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teen, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) BioEssays 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku, K. D. and Goldberg, R. B. *Plant Cell* 1:1079-1093, 1989), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis, p26*, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608, 144; 5,604,121; 5,569,597; 5,466,785; 5,399,680; 5,268, 463; 5,608,142 and 6,177,611, herein incorporated by reference.

The above list of promoters is not meant to be limiting. Any appropriate promoter can be used in the embodiments.

The gene expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

By "signal sequence" it is intended a sequence that is known or suspected to result in cotranslational or post-translational peptide transport across the cell membrane. In eukaryotes, this typically involves secretion into the Golgi apparatus, with some resulting glycosylation. Novel pesticidal proteins of bacteria are often synthesized as protoxins, which are protolytically activated in the gut of the target pest (Chang, (1987) *Methods Enzymol.* 153:507-516). In some embodiments, the signal sequence is located in the native sequence or may be derived from a sequence of the embodiments. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. In particular, table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

In other embodiments the expressed polynucleotide sequence may be targeted to the chloroplast, and may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Suitable chloroplast transit peptides (CTP) are well known to one skilled in the art including chimeric CTPs comprising but not limited to, an N-terminal domain, a central domain or a C-terminal domain from a CTP from *Oryza sativa* 1-deoxy-D xyulose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type. Other CTPs suitable for use with the polynucleotides of the subject disclosure include the TraP nucleotide sequences as described in WO 2013116700, WO 2013116758, WO 2013116764, WO 2013116768, WO 2013116773, and WO 2017031211 herein incorporated by reference in their entirety.

In some embodiments, the termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

In other embodiments the recombinant gene expression cassette is operably linked to an *Agrobacterium* T-DNA border. In accordance with one embodiment the recombinant gene cassette further comprises a first and second T-DNA border, wherein the first T-DNA border is operably linked to one end of a gene construct, and the second T-DNA border is operably linked to the other end of a gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence of the polynucleotide encoding the IRDIG37126 polypeptide or variant thereof. In another embodiment, the first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In an embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence of the polynucleotide encoding the IRDIG37126 polypeptide or variant thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence of the polynucleotide encoding the IRDIG37126 polypeptide or variant thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence of the polynucleotide encoding the IRDIG37126 polypeptide or variant thereof.

Transgenes of interest may be stacked with the IRDIG37126 polypeptide or variant thereof of the subject disclosure. Exemplary transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene/heterologous coding sequence of the polynucleotide encoding the IRDIG37126 polypeptide or variant thereof is further stacked with at least one other transgene/heterologous coding sequence encoding a selectable marker or a gene product conferring insecticidal resistance, herbicide tolerance, small RNA expression, nitrogen use efficiency, water use efficiency, or nutritional quality.

1. Insect Resistance

Various insect resistance genes can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing an insect resistance gene. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry/Ab(truncated); cry1Ab Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing a herbicide tolerance gene. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be can be can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing an agronomic trait gene. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing a DNA binding gene. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing a small RNA sequence. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be can be further stacked with the polynucleotide encoding the IRDIG37126 polypeptide or variant thereof. The gene expression cassette encoding the polynucleotide encoding the IRDIG37126 polypeptide or variant thereof can be operably linked with at least one other gene expression cassette containing a reporter gene. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non *Agrobacterium* bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or green fluorescent protein genes) that may be present on the recombinant nucleic acid constructs. Such selection and screening methodologies are well known to those skilled in the art. Molecular confirmation methods that can be used to identify transgenic plants are known to those with skill in the art.

Transgenic Plants

In an embodiment, a plant, plant tissue, plant seed, or plant cell comprises a polynucleotide encoding the IRDIG37126 polypeptide or variant thereof. In one embodiment a plant, plant tissue, or plant cell comprises the polynucleotide encoding the IRDIG37126 polypeptide or variant thereof of a sequence selected from SEQ ID NO:1 or SEQ ID NO:25-36, or a sequence that has 80%, 85%, 90%, 95% or 99.5% sequence identity with a sequence selected from SEQ ID NO:1 or SEQ ID NO:25-36. In an embodiment, a plant, plant tissue, plant seed, or plant cell comprises a gene expression cassette comprising the polynucleotide encoding the IRDIG37126 polypeptide of a sequence selected from SEQ ID NO:1 or SEQ ID NO:25-36, or a sequence that has 80%, 85%, 90%, 95% or 99.5% sequence identity with a sequence selected from SEQ ID NO:1 or SEQ ID NO:25-36. In an embodiment, a plant, plant tissue, or plant cell comprises the IRDIG37126 polypeptide or variant thereof. In one embodiment a plant, plant tissue, plant seed, or plant cell comprises the IRDIG37126 polypeptide, wherein the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an embodiment, a plant, plant tissue, plant seed, or plant cell comprises a gene expression cassette comprising a polynucleotide that expresses the IRDIG37126 polypeptide, wherein the IRDIG37126 polypeptide comprises a polynucleotide sequence having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an illustrative embodiment, a plant, plant tissue, plant seed, or plant cell comprises a gene expression cassette comprising the polynucleotide encoding the IRDIG37126 polypeptide further comprising at least one other transgene or heterologous coding sequence, wherein the transgene or heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In some instances, more than one transgene/heterologous coding sequence may be incorporated into the genome of the transformed host plant cell. Such is the case when more than one protein-encoding DNA segment is incorporated into the genome of such a plant. In certain situations, it may be desirable to have one, two, three, four, or even more insecticidal proteins or other insecticidal IRDIG proteins or nucleic acids incorporated and stably expressed in the transformed transgenic plant.

In another embodiment the plant, plant tissue, plant seed, or plant cell comprising the polynucleotide encoding the IRDIG37126 polypeptide or variant thereof is a dicotyledonous or monocotyledonous plant, seed, cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*).

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

In an embodiment, a plant, plant tissue, or plant cell according to the methods disclosed herein can be a monocotyledonous plant. The monocotyledonous plant, plant tissue, or plant cell can be, but not limited to various turf grasses, wheat, corn, rice, barley, oats, and species of the genus *Brachypodium*.

In accordance with one embodiment the gene expression cassette comprising the polynucleotide encoding the IRDIG37126 polypeptide or variant thereof is incorporated into the genome of the plant, plant tissue, plant seed, or plant cell. One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed. For example, two different transgenic plants can be mated to produce offspring that contain two independently segregating transgenes/heterologous coding sequences. Selfing of appropriate progeny can produce plants that are homozygous for both transgenes/heterologous coding sequences that encode a polypeptide of interest. Back-crossing to a parental plant and out-crossing with a non-transgenic plant are also contemplated. The result of back-crossing produces a transgenic progeny plant that is homozygous for transgenes/heterologous coding sequences. A homozygous transgenic plant can be obtained by sexually mating (selfing) an independent segregant transgenic plant that contains a single added gene, germinating some of the seed produced and analyzing the resulting plants produced for enhanced insecticidal activity relative to a control (native, non-transgenic) or an independent segregant transgenic plant.

The present disclosure also encompasses seeds of the transgenic plants described above, wherein the seed has the transgene/heterologous coding sequence of the polynucleotide encoding the IRDIG37126 polypeptide or variant thereof as provided in the subject disclosure. The present disclosure further encompasses the progeny, clones, callous cultures, cell lines or cells of the transgenic plants described above wherein said progeny, clone, callous cultures, cell line or cell has the transgene/heterologous coding sequence or gene construct containing the polynucleotides of the subject disclosure.

The present disclosure also encompasses the regeneration, development, and production of plants from transformants or from various transformed explants. Such methodology is well known in the art. This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the transgene/heterologous coding sequence of the polynucleotide encoding the IRDIG37126 polypeptide or variant thereof can be achieved by methods well known in the art. In this procedure, transformants are cultured in the presence of a selection agent and in a medium that induces the regeneration of shoots in the plant strain being transformed as described. This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

In some instances the regenerated plants are self-pollinated to provide homozygous transgenic plants, as discussed before. Otherwise, pollen obtained from the regenerated plants is crossed to seed-grown plants of agronomically important, such as inbred lines. Conversely, pollen from plants of those important lines is used to pollinate regenerated plants. A transgenic plant of the subject disclosure containing the transgene/heterologous coding sequence of the polynucleotide encoding the IRDIG37126 polypeptide or variant thereof is produced using methods well known to one skilled in the art.

A transgenic plant of the subject disclosure contains a stably integrated transgene/heterologous coding sequence that encodes the transgene/heterologous coding sequence of the polynucleotide encoding the IRDIG37126 polypeptide or variant thereof. In an embodiment the transgenic plant is an independent segregant and can transmit that gene and its activity to its progeny. In further embodiments the transgenic plant is homozygous for that gene, and transmits that gene to all of its offspring through sexual mating. Seed from a transgenic plant may be grown in the crop field or greenhouse, and resulting sexually mature transgenic plants are self-pollinated to generate true breeding plants. The progeny from these plants become true breeding lines that are evaluated for, by way of example, increased insecticidal capacity against insects, for example in the crop field, under a range of environmental conditions. Such methodology will find particular utility in the creation of transgenic plants of commercial interest.

The present disclosure also encompasses the cultivation of transgenic plants described above, wherein the transgenic plant has the transgene/heterologous coding sequence of the polynucleotide encoding the IRDIG37126 polypeptide or variant thereof provided in the subject disclosure. Accordingly, such transgenic plants may be engineered to, inter alia, have one or more desired traits or transgenic events containing the gene regulatory elements of the subject disclosure, by being transformed with nucleic acid molecules according to the disclosure, and may be cropped or cultivated by any method known to those of skill in the art.

In a Microbial Cell

In an embodiment, a microbial cell comprises a polynucleotide encoding the IRDIG37126 polypeptide or variant thereof. In one embodiment a microbial cell comprises the polynucleotide encoding the IRDIG37126 polypeptide of a sequence selected from SEQ ID NO:1 or SEQ ID NO:25-36 or a sequence that has 80%, 85%, 90%, 95% or 99.5% sequence identity with a sequence selected from SEQ ID NO:1 or SEQ ID NO:25-36. In an embodiment, a microbial cell comprises a gene expression cassette comprising the polynucleotide encoding the IRDIG37126 polypeptide of a sequence selected from SEQ ID NO:1 or SEQ ID NO:25-36, or a sequence that has 80%, 85%, 90%, 95% or 99.5% sequence identity with a sequence selected from SEQ ID NO:1 or SEQ ID NO:25-36. In an embodiment, a microbial cell comprises the IRDIG37126 polypeptide. In one embodiment a microbial cell comprises the IRDIG37126 polypeptide, wherein the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an embodiment, a microbial cell comprises a gene expression cassette comprising a polynucleotide that encodes the IRDIG37126 polypeptide, wherein the IRDIG37126 polypeptide comprises a polypeptide sequence having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In further embodiments, the microbial cell may be a bacteria, baculovirus, algae, yeast, or a fungi cell. Non-limiting examples of bacterial cells include *Pseudomonas, Bacillus* (including *B. megaterium, B. subtilis*, and *B. thuringiensis*), *Agrobacterium, Escherichia*, or other species of the Enterobacteraceae.

The present disclosure also encompasses microbial host cells which express a polynucleotide encoding the IRDIG37126 polypeptide or variant thereof, in the soluble fraction, inclusion bodies or crystals, culture supernatant, disrupted cells, cell extracts, lysates, homogenates, and the like. The bacterial host cells may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing the IRDIG37126 polypeptide or variant thereof are well-known to those of skill in the art of microbial protein isolation and purification. In certain embodiments, the proteins may be purified, concentrated, admixed with other reagents, or processed to a desired final form. In some embodiments, the composition will comprise from about 1% to about 90% by weight of the protein, and in other embodiments from about 5%, to about 50% by weight.

The present disclosure also encompasses protein compositions that are prepared by a process which comprises the steps of culturing a microbial cell. The microbial cells are engineered to express a polynucleotide encoding the IRDIG37126 polypeptide or variant thereof under conditions effective to produce such a protein, and then obtaining the protein from the cell. The obtaining of such a protein may further include purifying, concentrating, processing, or mixing the protein with one or more reagents. In some embodiments, the IRDIG37126 polypeptide or variant thereof is obtained in an amount of from between about 1% to about 90% by weight and in other embodiments from about 5% to about 50% by weight.

Composition

In an embodiment, the subject disclosure includes a composition comprising the IRDIG37126 polypeptide or variant thereof. In one embodiment a composition comprises the polynucleotide encoding the IRDIG37126 polypeptide of a sequence selected from SEQ ID NO:1 or a sequence that has 80%, 85%, 90%, 95% or 99.5% sequence identity with a sequence selected from SEQ ID NO:1 or SEQ ID NO:25-36. In an embodiment, a composition comprises a gene expression cassette comprising the polynucleotide encoding the IRDIG37126 polypeptide or variant thereof of a sequence selected from SEQ ID NO:1 or SEQ ID NO:25-36, or a sequence that has 80%, 85%, 90%, 95% or 99.5% sequence identity with a sequence selected from SEQ ID NO:1 or SEQ ID NO:25-36. In an embodiment, a composition comprises the IRDIG37126 polypeptide or variant thereof. In one embodiment the composition comprises the IRDIG37126 polypeptide, wherein the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24.

In certain embodiments, the subject disclosure relates to a method of preparing a composition comprising the IRDIG37126 polypeptide or variant thereof. Such a method generally involves the steps of culturing a microbial cell which expresses the IRDIG37126 polypeptide or variant thereof under conditions effective to produce the protein, and then obtaining the protein so produced. Prokaryotic host cells including Gram-negative cells such as *E. coli, Pseudomonas fluorescens* and related Enterobacteraceae, or Gram-positive cells such as *Bacillus* spp. (including *B. megaterium, B. subtilis,* and *B. thuringiensis*) and the like are all contemplated to be useful in the preparation of the IRDIG37126 polypeptide or variant thereof of the subject disclosure.

Alternatively, the compositions may be prepared by native or recombinant bacterial expression systems in vitro and isolated for subsequent crop field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the protein and apply solutions, suspensions, or collodial preparations of such crystals and/or spores as the active bioinsecticidal composition.

The composition comprising the IRDIG37126 polypeptide or variant thereof described may be made by formulating the bacterial cell, crystal and/or spore suspension, or isolated protein component with the desired agriculturally-acceptable carrier. The composition comprising the IRDIG37126 polypeptide or variant thereof may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques. Likewise the formulation may be mixed with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

In some embodiments the composition comprising the IRDIG37126 polypeptide or variant thereof can be applied in the form of compositions and can be applied to the crop field or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying the composition comprising the IRDIG37126 polypeptide or variant thereof include leaf application, seed coating and soil application. Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art. The compositions of the subject disclosure are applied to the environment of the target insect, typically onto the foliage and in the rhizosphere (the soil surrounding plant roots) of the plant or crop to be protected, by conventional methods, for example by spraying.

In further embodiments of the subject disclosure, the compositions comprising the IRDIG37126 polypeptide or variant thereof of the subject disclosure will find particular utility as insecticides for topical or systemic application to crops, grasses, fruits and vegetables, and ornamental plants. In an embodiment, the composition comprises an oil flowable suspension of bacterial cells which expresses a novel protein disclosed herein. For example, the bacterial host cell expresses the novel nucleic acid segments disclosed herein and produce a protein.

In another embodiment, the composition comprising the IRDIG37126 polypeptide or variant thereof is provided as a water dispersible granule. This granule comprises bacterial cells which expresses a novel protein as disclosed herein. Exemplary bacterial cells include *B. thurigiensis, B. megaterium, B. subtilis, E. coli*, or *Pseudomonas* spp. cells that have been transformed with a DNA segment disclosed herein and expressing the protein are also contemplated to be useful.

In a further embodiment, the composition comprising the IRDIG37126 polypeptide or variant thereof is provided as a powder, dust, pellet, or collodial concentrate. This form of composition comprises bacterial cells which expresses a novel protein as disclosed herein. Such dry forms of the insecticidal compositions may be formulated to dissolve immediately upon wetting, or alternatively, dissolve in a controlled-release, sustained release, or other time-dependent manner. Exemplary bacterial cells include *B. thurigiensis, B. megaterium, B. subtilis, E. coli*, or *Pseudomonas* spp. cells that have been transformed with a DNA segment disclosed herein and expressing the protein are also contemplated to be useful.

In yet another embodiment, the composition comprising the IRDIG37126 polypeptide or variant thereof is provided as an aqueous suspension of bacterial cells such as those described above which express the protein. Such aqueous suspensions may be provided as a concentrated stock solution which is diluted prior to application, or alternatively, as a diluted solution ready-to-apply.

The composition of the subject disclosure may be employed in the method of the disclosure singly or in combination with other compounds, including and not limited to other pesticides. These methods may also be used in conjunction with other treatments such as surfactants, detergents, polymers or time-release formulations. The insecticidal compositions of the present disclosure may be formulated for either systemic or topical use.

In other embodiments of the subject disclosure, the plants can also be treated by IRDIG37126 polypeptide or variant thereof with one or more chemical compositions, including one or more herbicide, insecticides or fungicides.

Regardless of the method of application or the content of the composition, the amount of the active component(s) are applied at an insecticidally-effective amount, which will vary depending on such factors as, for example, the specific insects to be controlled, the specific plant or crop to be treated, the environmental conditions, and the method, rate, and quantity of application of the insecticidally-active composition. The number of applications and the rate of application depend on the intensity of infestation by the corresponding pest. Likewise, the strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the composition, as well as the particular formulation contemplated.

The concentration of composition which is used for environmental, systemic, or soil application will vary widely depending upon the nature of the particular formulation, means of application, environmental conditions, and degree of biocidal activity. Typically, the composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. In other instance, the composition may be administered to a particular plant or target area in one or more applications as needed, with a typical crop field application rate per hectare ranging on the order of from about 50 g to about 500 g of active ingredient, or of from about 500 g to about 1000 g, or of from about 1000 g to about 5000 g or more of active ingredient.

Commodity Product

In an embodiment, the subject disclosure includes a commodity product. In certain aspects the commodity product is produced within the transgenic plant of the subject disclosure. Exemplary commodity products include protein concentrate, protein isolate, grain, meal, flour, oil, or fiber. In other examples such commodity products may include whole or processed seeds, animal feed containing transgenic plants of the subject disclosure or transgenic plant by-products, oil, meal, flour, starch, flakes, bran, biomass and stover, and fuel products and fuel by-products when made from transgenic plants or plant parts.

Furthermore, the commodity products may be sold to consumers and may be viable or nonviable. Nonviable commodity products include but are not limited to nonviable seeds; processed seeds, seed parts, and plant parts; seeds and plant parts processed for feed or food, oil, meal, flour, flakes, bran, biomasses, and fuel products. Viable commodity products include but are not limited to seeds, plants, and plant cells. The plants comprising the polynucleotides and polypeptides of the subject disclosure can thus be used to manufacture any commodity product typically acquired from such a transgenic crop plant.

Method of Expressing a Transgene

In an embodiment, a method of expressing the polynucleotide sequence of interest within a plant comprises growing a plant containing a gene encoding the IRDIG37126 polypeptide or variant thereof operably linked to at least one regulatory element or a polylinker sequence. In an embodiment the gene encoding the IRDIG37126 polypeptide consists of a sequence selected from SEQ ID NO:1 or SEQ ID NO:25-36 or a sequence that has 80%, 82.5%, 85%, 87.5%, 90%, 91%, 92%, 93%, 94%, 95%, 96%, 97%, 98%, 99% or 99.5% sequence identity with a sequence selected from SEQ ID NO:1 or SEQ ID NO:25-36. In another embodiment the gene encoding the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an embodiment, a method of expressing at least one polynucleotide sequence of interest in a plant tissue or plant cell comprising culturing a plant tissue or plant cell containing a gene encoding the IRDIG37126 polypeptide operably linked to at least one transgene. In a further embodiment, a method of expressing a gene encoding the IRDIG37126 polypeptide or variant thereof contained within a plant results in protecting the plant from an insect pest.

In an embodiment, a method of expressing the polynucleotide sequence of interest within a plant comprises growing a plant containing a gene expression cassette comprising a gene encoding the IRDIG37126 polypeptide or variant thereof operably linked to at least one regulatory element or a polylinker sequence. In an embodiment the gene expression cassette comprising a gene encoding the IRDIG37126 polypeptide consists of a sequence selected from SEQ ID NO:1 or SEQ ID NO:25-36 or a sequence that has 80%, 82.5%, 85%, 87.5%, 90%, 91%, 92%, 93%, 94%, 95%, 96%, 97%, 98%, 99% or 99.5% sequence identity with a sequence selected from SEQ ID NO:1 or SEQ ID NO:25-36. In another embodiment the gene expression cassette comprising a gene encoding the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an embodiment, a method of expressing at least one polynucleotide sequence of interest in a plant tissue or plant cell comprises culturing a plant tissue or plant cell containing a gene expression cassette comprising a gene encoding the IRDIG37126 polypeptide or variant thereof operably linked to at least one transgene. In a further embodiment, the method of expressing a gene encoding the IRDIG37126 polypeptide from a gene expression cassette contained within a plant results in protecting the plant from an insect pest.

In an embodiment, a method of expressing the polynucleotide sequence of interest within a microorganism comprises growing a microorganism containing a gene expression cassette comprising a gene encoding the IRDIG37126 polypeptide or variant thereof operably linked to at least one regulatory element or a polylinker sequence. In an embodiment the gene expression cassette comprising a gene encoding the IRDIG37126 polypeptide consists of a sequence selected from SEQ ID NO:1 or SEQ ID NO:25-36 or a sequence that has 80%, 82.5%, 85%, 87.5%, 90%, 91%, 92%, 93%, 94%, 95%, 96%, 97%, 98%, 99% or 99.5% sequence identity with a sequence selected from SEQ ID NO:1 or SEQ ID NO:25-36. In another embodiment the gene expression cassette comprising a gene encoding the IRDIG37126 polypeptide comprises a polypeptide having at least 80%, 82.5%, 85%, 87.5%, 90%, 91%, 92%, 93%, 94%, 95%, 96%, 97%, 98%, 99%, 99.5%, 99% or 100% identity to the amino acid sequence of SEQ ID NO:2 or SEQ ID NO:13-24. In an embodiment, a method of expressing at least one polynucleotide sequence of interest in microorganism comprises culturing a plant tissue or plant cell containing a gene expression cassette comprising a gene encoding the IRDIG37126 polypeptide or variant thereof operably linked to at least one transgene. In a further embodiment, the method of expressing a gene encoding the IRDIG37126 polypeptide or variant thereof from a gene expression cassette contained within a microorganism results in producing a protein with insecticidal activity.

In some embodiment the gene encoding the IRDIG37126 polypeptide or variant thereof is expressed in the plant, plant cell, plant part, or plant seed in a constitutive manner. In an aspect of such an embodiment, the constitutive expression directs transcription in most or all tissues at all time. Accordingly, the constitutive expression is more or less at a steady state level throughout development. In other embodiments, the gene encoding the IRDIG37126 polypeptide or variant thereof is expressed in the plant, plant cell, plant part, or plant seed in a tissue preferred manner. In an aspect of such an embodiment, the tissue preferred expression is expressed in only certain tissue types or at certain times during development.

Insecticidal Activity

In an embodiment, the subject disclosure provides the IRDIG37126 polypeptide or variant thereof which confers insecticidal activity. Also provided are the polynucleotide sequences that encode the IRDIG37126 polypeptide or variant thereof. The IRDIG37126 protein resulting from translation of these polynucleotide sequences allows for the control or death of insect pests that ingest the IRDIG37126 polypeptide or variant thereof. In an aspect of this embodiment the IRDIG37126 polypeptide or variant thereof is orally active in providing insecticidal activity. In further aspects, the IRDIG37126 polypeptide or variant thereof may be utilized to provide insecticidal activity against insect pests, in economically important agronomic, forest, greenhouse, nursery ornamentals, food and fiber, public and animal health, domestic and commercial structure, household and stored product pests. In other aspects the IRDIG37126 polypeptide or variant thereof provides toxic insecticidal activity against one or more insect pests. Examples of such insect pests include, but is not limited to, members of the Lepidoptera, Diptera, Hemiptera and Coleoptera orders or the Nematoda phylum or a protein that has homology to such a protein In some embodiments, the insecticidal activity is provided against Lepidopteran, Dipteran, Heteropteran, Nematode, Hemiptera or Coleopteran pests. In further aspects of this embodiment, the Lepidopteran, Dipteran, Heteropteran, Nematode, Hemiptera or Coleopteran pests may be killed or reduced in numbers by the methods of the disclosure. In further embodiments the insecticidal activity is provided against Soybean Looper such that the Soybean Looper pest may be killed or reduced in numbers by the methods of the disclosure. In other embodiments the insecticidal activity is provided against stink bug such that the stink bug pest may be killed or reduced in numbers by the methods of the disclosure.

In other embodiment of the subject disclosure, methods are provided for producing the polypeptides and for using IRDIG37126 polypeptide or variant thereof of to control, inhibit growth or kill a Lepidopteran, Coleopteran, Nematode, Hemipteran and/or Dipteran pest. In some embodiments, the transgenic plants of the subject disclosure are engineered to express one or more polynucleotides encoding the IRDIG37126 polypeptide or variant thereof as disclosed herein. In various embodiments, the transgenic plants further comprise one or more additional genes for insect resistance, for example, one or more additional genes for controlling Coleopteran, Lepidopteran, Hemipteran, Dipteran, and/or Nematode pests.

Exemplary IRDIG37126 polypeptide or variant thereof find use in controlling, inhibiting growth or killing Lepidopteran and Hemipteran pest populations and for producing compositions with insecticidal activity against such insects. Included as insect pests of interest are adults and nymphs. Insect pests of interest include, but are not limited to, the superfamily of stink bugs and other related insects including, but not limited to, species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid), and the family Cydnidae (*Scaptocoris castanea*—Root stink bug) and Lepidoptera species including but not limited to: Soybean Looper, e.g., *Pseudoplusia includens* or *Chrysodeixis includens*.

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schïffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp.; and *Cimicidae* spp.

Methods for measuring insecticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests. For each substance or organism, the insecticidally-effective amount is determined empirically for each pest affected in a specific environment.

Methods for Inhibiting Growth or Killing an Insect Pest and Controlling an Insect Population In some embodiments methods are provided for inhibiting growth or killing an insect pest, comprising contacting the insect pest with an insecticidally-effective amount of a recombinant IRDIG37126 polypeptide. In some embodiments methods are provided for inhibiting growth or killing an insect pest, comprising contacting the insect pest with an insecticidally-effective amount of a recombinant pesticidal protein of SEQ ID NO:2 or a variant thereof.

In some embodiments methods are provided for controlling an insect pest population, comprising contacting the insect pest population with an insecticidally-effective amount of a recombinant IRDIG37126 polypeptide or variant thereof. In some embodiments methods are provided for controlling an insect pest population, comprising contacting the insect pest population with an insecticidally-effective amount of a recombinant pesticidal protein of SEQ ID NO:2 or a variant thereof.

In some embodiments methods are provided for controlling an insect pest population resistant to a pesticidal protein, comprising contacting the insect pest population with an insecticidally-effective amount of a recombinant IRDIG37126 polypeptide or variant thereof. In some embodiments methods are provided for controlling an insect pest population resistant to a pesticidal protein, comprising contacting the insect pest population with an insecticidally-effective amount of a recombinant pesticidal protein of SEQ ID NO:2 or a variant thereof.

In some embodiments methods are provided for protecting a plant from an insect pest, comprising expressing in the plant or cell thereof a recombinant IRDIG37126 polypeptide or variant thereof. In some embodiments methods are provided for protecting a plant from an insect pest, comprising expressing in the plant or cell thereof a recombinant pesticidal protein of SEQ ID NO:2 or variants thereof.

Insect Resistance Management (IRM) Strategies

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush for example, outlines two-toxin strategies, also called "pyramiding" or "stacking," for management of insecticidal transgenic crops. (The Royal Society. Phil.

Trans. R. Soc. Lond. B. (1998) 353:777-1786). Stacking or pyramiding of two different proteins each effective against the target pests and with little or no cross-resistance can allow for use of a smaller refuge. The U.S. Environmental Protection Agency requires significantly less (generally 5%) structured refuge of non-Bt corn be planted than for single trait products (generally 20%). There are various ways of providing the IRM effects of a refuge, including various geometric planting patterns in the crop fields and in-bag seed mixtures, as discussed further by Roush.

In some embodiments the IRDIG37126 polypeptide or variant thereofs of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, and the like.

Provided are methods of controlling Lepidoptera and/or Hemiptera insect infestation(s) in a transgenic plant that promote insect resistance management, comprising expressing in the plant at least two different insecticidal proteins having different modes of action.

In some embodiments the methods of controlling Lepidoptera and/or Hemiptera insect infestation in a transgenic plant and promoting insect resistance management the at least one of the insecticidal proteins comprise a IRDIG37126 polypeptide or variant thereof insecticidal to insects in the order Lepidoptera and/or Hemiptera.

In some embodiments the methods of controlling Lepidoptera and/or Hemiptera insect infestation in a transgenic plant and promoting insect resistance management the at least one of the insecticidal proteins comprises a protein of SEQ ID NO:2 or variants thereof, insecticidal to insects in the order Lepidoptera and/or Hemiptera.

In some embodiments the methods of controlling Lepidoptera and/or Hemiptera insect infestation in a transgenic plant and promoting insect resistance management comprise expressing in the transgenic plant a IRDIG37126 polypeptide or variant thereof and a Cry protein insecticidal to insects in the order Lepidoptera and/or Hemiptera having different modes of action.

In some embodiments the methods of controlling Lepidoptera and/or Hemiptera insect infestation in a transgenic plant and promoting insect resistance management comprise in the transgenic plant a protein of SEQ ID NO:2 or variants thereof and a Cry protein insecticidal to insects in the order Lepidoptera and/or Hemiptera having different modes of action.

Also provided are methods of reducing likelihood of emergence of Lepidoptera and/or Hemiptera insect resistance to transgenic plants expressing in the plants insecticidal proteins to control the insect species, comprising expression of a IRDIG37126 polypeptide or variant thereof insecticidal to the insect species in combination with a second insecticidal protein to the insect species having different modes of action.

Also provided are methods of reducing likelihood of emergence of Lepidoptera and/or Hemiptera insect resistance to transgenic plants expressing in the plants insecticidal proteins to control the insect species, comprising expression of a protein of SEQ ID NO:2 or variants thereof, insecticidal to the insect species in combination with a second insecticidal protein to the insect species having different modes of action.

Also provided are means for effective Lepidoptera and/or Hemiptera insect resistance management of transgenic plants, comprising co-expressing at high levels in the plants two or more insecticidal proteins toxic to Lepidoptera and/or Hemiptera insects but each exhibiting a different mode of effectuating its inhibiting growth or killing activity, wherein the two or more insecticidal proteins comprise a IRDIG37126 polypeptide or variant thereof and a Cry protein. Also provided are means for effective Lepidoptera and/or Hemiptera insect resistance management of transgenic plants, comprising co-expressing at high levels in the plants two or more insecticidal proteins toxic to Lepidoptera and/or Hemiptera insects but each exhibiting a different mode of effectuating its inhibiting growth or activity, wherein the two or more insecticidal proteins comprise a protein of SEQ ID NO:2 or variants thereof and a Cry protein.

In addition, methods are provided for obtaining regulatory approval for planting or commercialization of plants expressing proteins insecticidal to insects in the order Lepidoptera and/or Hemiptera, comprising the step of referring to, submitting or relying on insect assay binding data showing that the IRDIG37126 polypeptide or variant thereof does not compete with binding sites for Cry proteins in such insects. In addition, methods are provided for obtaining regulatory approval for planting or commercialization of plants expressing proteins insecticidal to insects in the order Lepidoptera and/or Hemiptera, comprising the step of referring to, submitting or relying on insect assay binding data showing that the protein of SEQ ID NO:2 or variant thereof does not compete with binding sites for Cry proteins in such insects.

The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb 1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1l or Cry1E (US2012/0324605).

Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

In a further embodiment, a method of expressing a gene encoding the IRDIG37126 polypeptide or variant thereof within a plant results in protecting the plant from an insect pest.

The following examples are provided to illustrate certain particular features and/or embodiments. The examples should not be construed to limit the disclosure to the particular features or embodiments exemplified.

EXAMPLES

Example 1: Methods for Enrichment of Microbial Species that Contain Hemipteran Active Proteins from Insect Specimens Insect sourcing and storage: Microorganisms were isolated from insects captured in a Mississippi soybean crop field and insects captured in a Dynatrap™ consumer light trap in Indiana. The insects from Mississippi were captured alive and immediately frozen on dry ice, while the insects from Indiana were mostly dead and decaying after being caught in the Dynatrap™ over a period of 4-6 weeks. The insects in the Dynatrap™ were predominantly flying insects like flies, moths, mosquitos, and beetles. The insects from Mississippi included a large number of grasshoppers, stink bugs, and caterpillars. All insects were stored at −80 C until immediately prior to enrichment.

Media preparation: Three different types of media were used for microbial enrichment. For *Pseudomonas* species enrichment, the Oxoid *Pseudomonas* Agar+CFC supplement (ThermoFisher, St. Louis, Mo.) was prepared according to the manufacturer's instruction. For *Bacillus cereus* group species enrichment, the Oxoid Brilliance *Bacillus Cereus* agar base (ThermoFisher, St. Louis, Mo.) was used according to the manufacturer's instructions with the exception that trimethoprim and polymyxin B sulfate were purchased individually and added to the sterilized media at a final concentration of 10 mg/L and 100,000 units/L, respectively. In addition, non-selective LB miller agar powder was also prepared with no additional supplements. Approximately 250 mL of sterilized media containing the indicated supplements was poured into 240 mm×240 mm trays and allowed to solidify.

Sample preparation for plating: About 1 to 5 grams of the insects obtained from Mississippi and Indiana were transferred into 50 mL conical tubes containing 3/16 inch steel beads and homogenized by vigorous shaking to a powder (for Indiana obtained insects) or a viscous homogenate (Mississippi obtained insects). To the homogenized insects approximately 25 mL of 1% w/v sodium chloride solution was added. The solution was vortexed briefly and then the steel beads and residual insect material was removed by filtering over cheesecloth. Additional 1% w/v sodium chloride solution was added to 50 mL, vortexed briefly, and then centrifuged at 5000 RPM for 10 minutes. The supernatant was discarded and the pellet was resuspended by pipetting up and down in ~5 mL of saline solution. This material was then immediately plated (for *Pseudomonas* enrichment) or heat pasteurized for spore former enrichment. Heat pasteurization was performed in 2 mL microcentrifuge tubes containing 1 mL of the resuspended pellet. The tubes were heated for 12 minutes at 80 C and 900 RPM in a thermomixer and then plated as quickly as possible (typically within 2-4 minutes of removal from the thermomixer).

Plating: Typically, 0.5 to 1 mL of appropriately diluted insect sample was plated onto the tray of solidified culture media. These conditions were optimized to obtain as many individual bacterial colonies as possible without forming a bacterial lawn on the plate. Plates were incubated at 28-30C for 16-24 hours before collection.

DNA extraction: Cells were collected by scraping the colonies directly from the surface of the agar plates into 50 mL conical tubes. DNA was extracted from the cells using a Power Lyzer Power Soil DNA™ isolation kit (Mo Bio Laboratories, Carlsbad, Calif.) according to the manufacturer's instructions. The fastprep sample preparation system was used for cell lysis with a speed of 6 m/s for 45 seconds. DNA quality was evaluated by agarose gel electrophoresis. The obtained DNA sample were submitted for sequencing on an Illumina NextSeq500™ using 2×150 paired end sequencing reagents according to the manufacturer's instructions.

Example 2: Sequencing and Identification of Novel Putative Hemipteran Active Insecticidal Proteins Data analysis: An Illumina sequencing library was prepared from each metagenomic DNA sample following standard procedures in the NGS COE. The libraries were pooled and sequenced using a 2×150 paired end Mid-output sequencing kit on a NextSeg500™ sequencer. Approximately 10-20 million paired end reads were generated per library and analyzed for the presence of potential hemipteran active insecticidal proteins using an in-house TBLASTN algorithm. Based on this search four reads out of 18 million were identified as belonging to a probable hemipteran active monalysin. More sequencing was performed on the enrichments with evidence of the probable hemipteran active monalysin to accumulate enough reads to determine the full sequence of the gene that was labeled as IRDIG37126. The polynucleotide sequence (SEQ ID NO:1) of the probable hemipteran active monalysin was obtained and translated to a polypeptide sequence (SEQ ID NO:2).

IRDIG37126 was compared to other known monalysin protein sequences. IRDIG37126 was found to have 79.7% identity to PIP-1 (polynucleotide sequence listing number 2 of U.S. Pat. No. 9,688,730, provided herein as SEQ ID NO:3) and 74.2% identity to the prototypical monalysin of IRDIG22274 (Genbank Acc. No. WP_011534324, provided herein as SEQ ID NO:4). See FIG. 1 for a protein alignment that was completed using the AlignX program of Vector NTI Advance v11 (Invitrogen; Carlsbad, Calif.). In addition, a phylogenetic tree of the IRDIG37126 protein sequence was completed to compare the novel protein with other known monalysin protein sequences as listed in Table 1. See FIG. 2 for a phylogenetic tree that was completed using the Geneious program version no.11 (Kearse, M., et al., (2012). Geneious Basic: an integrated and extendable desktop software platform for the organization and analysis of sequence data. Bioinformatics, 28(12), 1647-1649.). From these bioinformatics analysis, it was determined that the novel protein sequence of IRDIG37126 (SEQ ID NO:2) shared at most 80.8% sequence identity with a known monalysin protein sequence (Table 1).

TABLE 1

Percent sequence identity of IRDIG37126 (SEQ ID NO: 2) as compared to other known protein sequences.

| Sample name and description | Percent identity to IRDIG37126 (SEQ ID NO: 2) |
|---|---|
| Polynucleotide sequence listing number 4 of U.S. Pat. No. 9,688,730, provided herein as SEQ ID NO: 5 | 80.6% |
| Genbank Acc. No. WP_078473056.1, provided herein as SEQ ID NO: 6 | 80.1% |
| Genbank Acc. No. WP_020294695.1, provided herein as SEQ ID NO: 7 and described as IRDIG31502 | 80.8% |
| PIP-1, provided herein as SEQ ID NO: 3 | 79.7% |
| Polynucleotide sequence listing number 9 of U.S. Patent App. No. 20170175134, provided herein as SEQ ID NO: 8 | 79.9% |
| Polynucleotide sequence listing number 332 of U.S. Pat. No. 9,688,730, provided herein as SEQ ID NO: 9 | 76.0% |
| Polynucleotide sequence listing number 82 of U.S. Patent App. No. 20170175134, provided herein as SEQ ID NO: 10 | 77.1% |
| IRDIG22274, provided herein as SEQ ID NO: 4 | 74.2% |

Example 3: Evaluation of IRDIG37126 (SEQ ID NO:2) for Insecticidal Activity Against Neotropical Brown Stink Bug Protein expression and insect bioassays: The coding sequence of IRDIG37126 (SEQ ID NO:1) was cloned into the pMAL c5x vector with a N-terminal maltose binding protein expression tag. The protein was overexpressed in *Escherichia coli* and purified according to the manufacturer's instructions using amylose resin (New England Biolabs, Ipswich, Mass.). The isolated protein was then utilized in diet based bioaasay to assess the insecticidal activity of the protein against specific insect pests.

Figure 3:
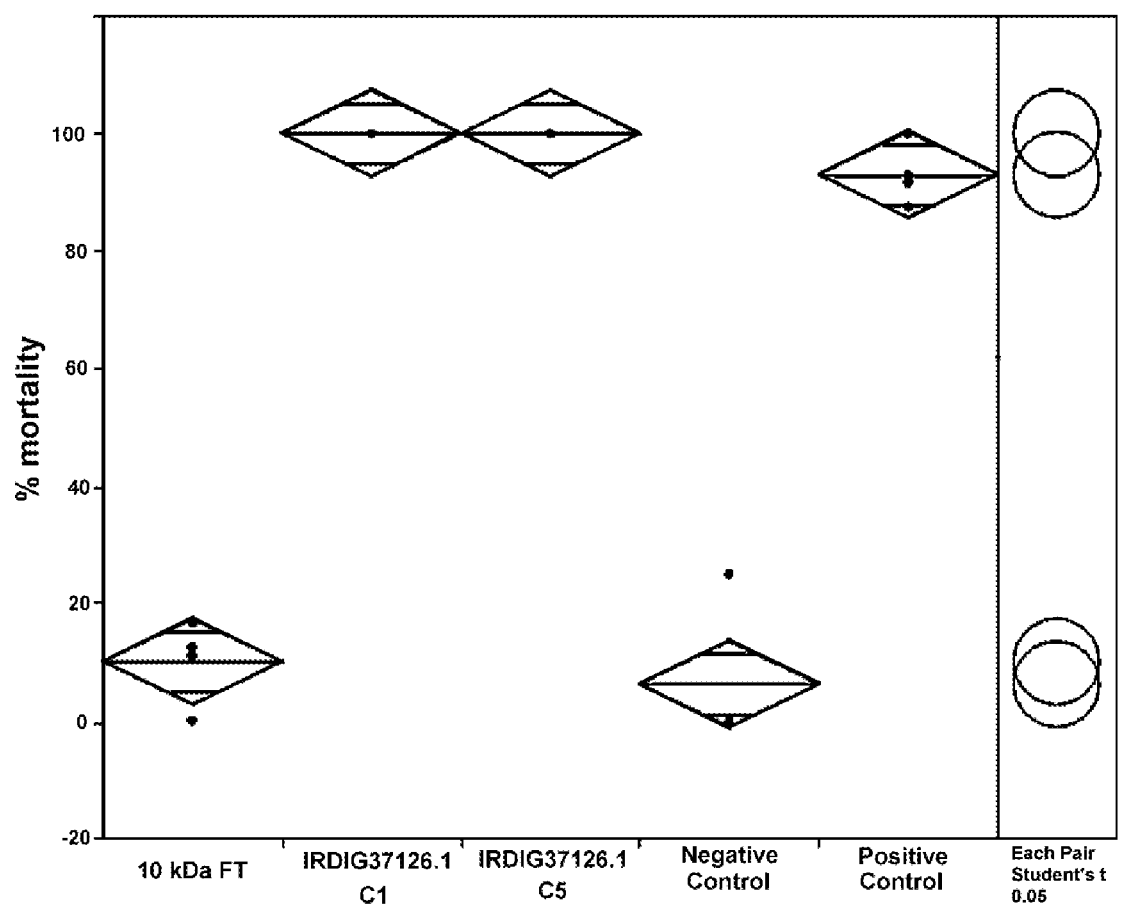
FIG. 3 provides a graph of the insect bioassay results for a high dose bioassay with the expressed IRDIG37126 protein. The Y-axis shows percent mortality average of four replicate wells. The IRDIG37126 protein was tested against BSB in the standard diet based bioassay. The samples tested include; 10 kDa FT (buffer control), IRDIG37126.1 C1 (IRDIG37126.1 colony one protein prep), IRDIG37126.1 C5 (IRDIG37126.1 colony five protein prep), Negative Control (diet only), and Positive Control (IRDIG31502 at 1000 ppm final concentration).

The eluted IRDIG37126 protein was tested against the hemipteran insect species, *Euschistus servus* that is commonly known as the brown stink bug (BSB), at a high dose and found to be active (FIG. 3, Table 2). A high-dose feeding bioassay was completed, where 2500 ppm of the purified protein was applied to the diet of BSB in a 24 well plate set up. Second instar nymphs were placed in each well to feed for 6 days. After this time period the BSB larvae were assessed for mortality and compared to negative and positive controls. These results indicated that the IRDIG37126 protein of SEQ ID NO:2 provided significant levels of mortality against BSB. For the first time, the IRDIG37126 protein was shown to confer insecticidal activity by controlling or killing insect pests that ingested the IRDIG37126 protein.

TABLE 2

Activity of IRDIG37126 (SEQ ID NO: 2) against Hemipteran insect pests in a high-dose feeding bioassay.

| Sample | No. of Insects Alive | No. of Insects Dead | Percent Mortality |
|---|---|---|---|
| IRDIG37126 | 0 | 68 | 100.0 |
| Buffer Control | 28 | 3 | 9.7 |
| Water (Negative Control) | 33 | 2 | 5.7 |
| IRDIG31502 (Positive Control) | 3 | 40 | 93.0 |

Figure 4:
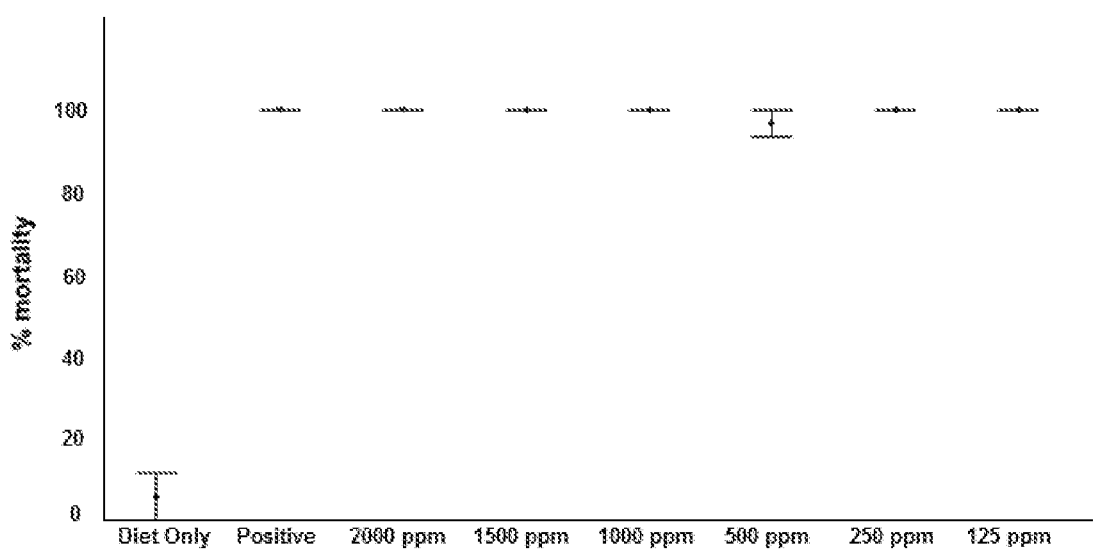
Figure 5:
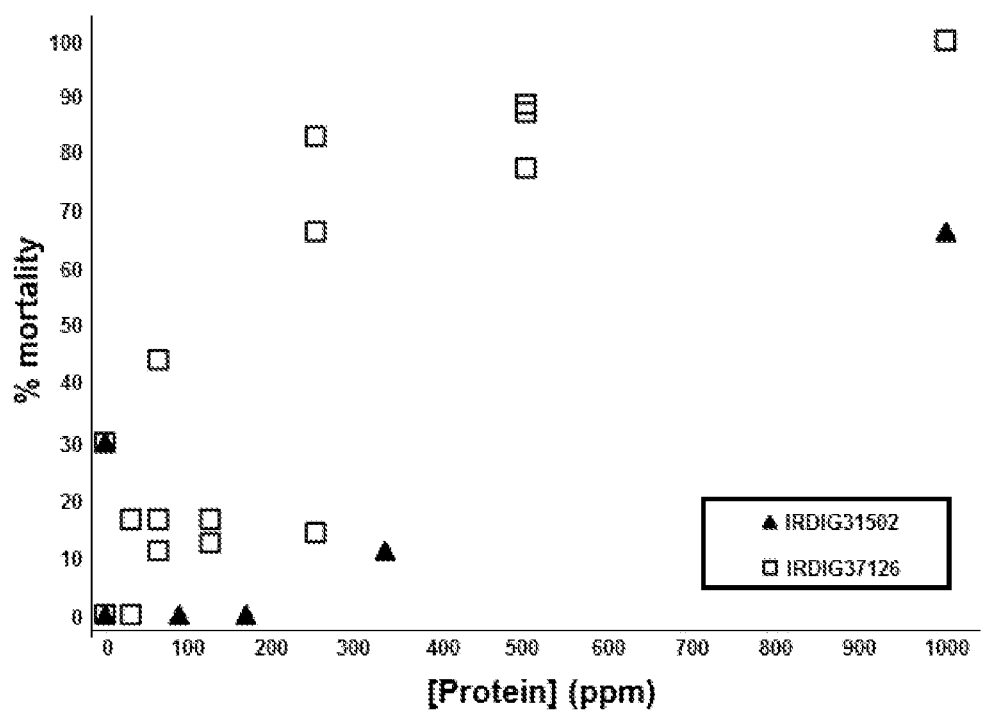

Next, the eluted IRDIG37126 protein was submitted to bioassay to generate a dose response curve (Table 3, FIG. 4, and FIG. 5). In one experiment the protein was active at all doses tested (lowest dose 125 ppm). In these experiments doses of the IRDIG37126 protein were tested at 125 ppm, 250 ppm, 500 ppm, 1000 ppm, 1500 ppm, and 2000 ppm. Each of these concentrations resulted in 100% mortality in BSB. In a second experiment the eluted IRDIG37126 protein showed greater than 50% mortality of BSB when applied to the bioassay diet at 250 ppm. Furthermore, the eluted IRDIG37126 protein resulted in higher BSB activity than IRDIG31502 (the positive control protein) at all concentrations that were tested. These results further indicate that the IRDIG37126 protein of SEQ ID NO:2 provided significant levels of mortality against BSB. Again, the IRDIG37126 protein was shown to confer insecticidal activity by controlling or killing insect pests that ingested the IRDIG37126 protein.

TABLE 3

Activity of IRDIG37126 (SEQ ID NO: 2) against hemipteran insect pests in a dose response curve feeding bioassay.

| Protein | Dose (ppm) | No. of Insects Alive | No. of Insects Dead | Percentage Mortality |
|---|---|---|---|---|
| Diet Only | 0 | 7 | 0 | 0.00 |
| Diet Only | 0 | 7 | 3 | 0.30 |
| IRDIG31502 | 1000 | 2 | 4 | 0.67 |
| IRDIG31502 | 167 | 10 | 0 | 0.00 |
| IRDIG31502 | 333 | 8 | 1 | 0.11 |
| IRDIG31502 | 88 | 8 | 0 | 0.00 |
| IRDIG37126 | 1000 | 0 | 10 | 1.00 |
| IRDIG37126 | 1000 | 0 | 10 | 1.00 |
| IRDIG37126 | 1000 | 0 | 8 | 1.00 |
| IRDIG37126 | 500 | 1 | 7 | 0.88 |
| IRDIG37126 | 500 | 1 | 8 | 0.89 |
| IRDIG37126 | 500 | 2 | 7 | 0.78 |
| IRDIG37126 | 250 | 6 | 1 | 0.14 |
| IRDIG37126 | 250 | 2 | 4 | 0.67 |
| IRDIG37126 | 250 | 1 | 5 | 0.83 |
| IRDIG37126 | 125 | 5 | 1 | 0.17 |
| IRDIG37126 | 125 | 7 | 1 | 0.13 |
| IRDIG37126 | 125 | 7 | 1 | 0.13 |
| IRDIG37126 | 63 | 5 | 1 | 0.17 |
| IRDIG37126 | 63 | 5 | 4 | 0.44 |
| IRDIG37126 | 63 | 8 | 1 | 0.11 |
| IRDIG37126 | 31 | 7 | 0 | 0.00 |
| IRDIG37126 | 31 | 5 | 1 | 0.17 |
| IRDIG37126 | 31 | 9 | 0 | 0.00 |

Example 4: Evaluation of IRDIG37126 (SEQ ID NO:2) for Insecticidal Activity Against Lepidopteran Species The IRDIG37126 was further tested against Lepidopteran species in a bioassay feeding experiment. A panel of the following Lepidopteran pests were used in the bioassay: soybean looper (SBL); European corn borer (ECB); corn earworm (CEW); fall armyworm (FAW); and cotton boll weevil (CBW) were tested. A high-dose feeding bioassay was completed, where 9 ug/cm2 of the purified protein was applied to the diet of BSB in a 96 well plate set up. Neonate larvae were placed in each well to feed for 5 days. After this time period the insect larvae were assessed for mortality and compared to negative and positive controls. These results indicated that although the IRDIG37126 protein of SEQ ID NO:2 did not have insecticidal activity against most of the Lepidopteran species tested, the IRDIG37126 protein of SEQ ID NO:2 did provide significant levels of mortality against soybean looper (SBL) as shown in Table 4.

TABLE 4

Activity of IRDIG37126 (SEQ ID NO: 2) against various lepidopteran pests at 9 ug/cm² in the diet based bioassay.

| Insect Tested | Sample Name | Wells Showing Insecticidal Activity | Total No. of Wells Tested | Hit Rate | Pass |
|---|---|---|---|---|---|
| SBL | IRDIG37126 | 16 | 16 | 1.000 | YES |
| SBL | Cry1Ca | 16 | 16 | 1.000 | YES |
| SBL | Caps Buffer | 3 | 16 | 0.188 | NO |
| SBL | BSA | 4 | 16 | 0.250 | NO |
| ECB | IRDIG37126 | 0 | 16 | 0.000 | NO |
| ECB | Cry1Ca | 2 | 16 | 0.125 | NO |
| ECB | Caps Buffer | 0 | 16 | 0.000 | NO |
| ECB | BSA | 2 | 16 | 0.125 | NO |
| CEW | IRDIG37126 | 1 | 16 | 0.063 | NO |
| CEW | Cry1Ca | 0 | 16 | 0.000 | NO |
| CEW | Caps Buffer | 0 | 16 | 0.000 | NO |
| CEW | BSA | 0 | 16 | 0.000 | NO |
| FAW | IRDIG37126 | 0 | 16 | 0.000 | NO |
| FAW | Cry1Ca | 0 | 16 | 0.000 | NO |
| FAW | Caps Buffer | 0 | 16 | 0.000 | NO |
| FAW | BSA | 0 | 16 | 0.000 | NO |
| CBW | IRDIG37126 | 0 | 16 | 0.000 | NO |
| CBW | Cry1Ca | 0 | 16 | 0.000 | NO |
| CBW | Caps Buffer | 0 | 16 | 0.000 | NO |
| CBW | BSA | 1 | 16 | 0.063 | NO |

Example 5: *Agrobacterium*-Mediated Transformation of a Heterologous Gene Expression Cassette Comprising the IRDIG37126 Gene Sequence Soybean may be transformed with a heterologous gene expression cassette comprising the IRDIG37126 gene sequence encoding SEQ ID NO:2 by utilizing the same techniques previously described in Example #11 or Example #13 of patent application WO 2007/053482.

Cotton may be transformed with a heterologous gene expression cassette comprising the IRDIG37126 gene sequence encoding SEQ ID NO:2 by utilizing the same techniques previously described in Examples #14 of U.S. Pat. No. 7,838,733 or Example #12 of patent application WO 2007/053482 (Wright et al.).

Canola may be transformed with a heterologous gene expression cassette comprising the IRDIG37126 gene sequence encoding SEQ ID NO:2 by utilizing the same techniques previously described in Example #26 of U.S. Pat. No. 7,838,733 or Example #22 of patent application WO 2007/053482 (Wright et al.).

Corn may be transformed with a heterologous gene expression cassette comprising the IRDIG37126 gene sequence encoding SEQ ID NO:2 by utilizing the same techniques previously described in Example #7 of U.S. Pat. No. 7,838,733 or Example #8 of patent application WO 2007/053482 (Wright et al.).

Wheat may be transformed with a heterologous gene expression cassette comprising the IRDIG37126 gene sequence encoding SEQ ID NO:2 by utilizing the same techniques previously described in Example #23 of patent application WO 2013/116700A1 (Lira et al.).

Rice may be transformed with a heterologous gene expression cassette comprising the IRDIG37126 gene sequence encoding SEQ ID NO:2 by utilizing the same techniques previously described in Example #19 of patent application WO 2013/116700A1 (Lira et al.).

Example 6: *Agrobacterium*-Mediated Transformation of a Heterologous Gene Expression Cassette Comprising the IRDIG37126 Gene Sequence In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18.

The Latin names for these and other plants are given below. It should be clear that other (non *Agrobacterium*) transformation techniques can be used to transform a heterologous gene expression cassette comprising the IRDIG37126 gene sequence encoding SEQ ID NO:2, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense,* and *frutescens*), Lettuce (*Lactuca sativa, perennis,* and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna,* and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon,* and other genera), Clover (*Trifolium*), Vetch (*Vicia*). Transformation of such plants, with genes operably linked to the *Glycine max* egg cell promoter, the *Glycine max* egg cell 5' UTR, the *Glycine max* egg cell 3' UTR and/or the *Glycine max* egg cell terminator, for example, is contemplated in embodiments of the subject disclosure.

Use of a heterologous gene expression cassette comprising the IRDIG37126 gene sequence encoding SEQ ID NO:2 can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Euca-* lyptus spp.), hickory (*Carya* spp.), maple (*Acer* spp.), oak (*Quercus* spp.), and pine (*Pinus* spp.).

Use of a heterologous gene expression cassette comprising the IRDIG37126 gene sequence encoding SEQ ID NO:2 can be deployed in ornamental and fruit-bearing species. Such applications are also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

Example 7: Molecular Analysis of Transgenic Plants Containing Stably Integrated Heterologous Gene Expression Cassette Comprising the IRDIG37126 Gene Sequence Molecular analysis of transformed plant tissues are performed on samples obtained from plants materials transformed with gene expression cassettes containing the heterologous gene expression cassette comprising the IRDIG37126 gene sequence to confirm the presence and copy number of a stably integrated heterologous gene expression cassette comprising the IRDIG37126 gene sequence and to quantitate the expressed quantity the IRDIG37126 protein being produced in the plant cell. Various assays are known in the art and can be utilized for molecular analysis of the heterologous gene expression cassette comprising the IRDIG37126 gene sequence within plant material.

Example 8: Insect Bioassay Analysis of Transgenic Plants Containing Stably Integrated Heterologous Gene Expression Cassette Comprising the IRDIG37126 Gene Sequence Bioactivity of transgenic plant material expressing the heterologous gene expression cassette comprising the IRDIG37126 gene sequence of the subject disclosure is demonstrated by known bioassay methods. See, e.g., Baum et al. (2007) Nat. Biotechnol. 25(11):1322-1326. The completion of these assays allows one to demonstrate efficacy of the IRDIG37126 protein, for example, by feeding various plant tissues or tissue pieces derived from a plant producing an insecticidal shRNA to target insects in a controlled feeding environment. Alternatively, extracts are prepared from various plant tissues derived from a plant producing the insecticidal IRDIG37126 protein, and the extracted nucleic acids are dispensed on top of artificial diets for bioassays. The results of such feeding assays are compared to similarly conducted bioassays that employ appropriate control tissues from host plants that do not produce a heterologous gene expression cassette comprising the IRDIG37126 gene sequence, or to other control samples. Growth and survival of target insects on the transgenic plant material expressing the IRDIG37126 protein is reduced compared to that of the control group.

Example 9: Evaluation of IRDIG37126 Variant Sequences for Insecticidal Activity Against Insects Production of IRDIG37126 variants: Sequence variants of IRDIG37126 (SEQ ID NO:13-24) were generated to assess the importance of various amino acid residues on insecticidal activity. FIGS. 6A, 6B, and 6C provide a sequence alignment of the variant sequences as compared to the IRDIG37126 protein of SEQ ID NO:2. Likewise, FIGS. 7A, 7B, and 7C provide the sequence identities for the variants as compared to the IRDIG37126 protein of SEQ ID NO:2 and to one another. The genus of IRDIG37126 variant sequences share at least 97.8% sequence identity with one another from the various mutations made at six different locations of the protein sequence (FIGS. 6A, 6B, and 6C). For single point mutations the coding sequence was modified to make the desired change and gene fragments encoding the variant proteins (SEQ ID NO:25-36) were purchased from Integrated DNA Technologies, Inc. (Skokie, Ill.). The gene fragments were cloned into the pMAL C5x vector with an N-terminal maltose binding protein expression tag. To evaluate double mutants, a library of two positions, D18 and D75, were selected and the wild type codon was replaced using a degenerate primer that contained the sequence VNN at positions D18 and D75. The character V corresponds to an equal mixture of bases G, A, and C at the position, while N refers to an equal mixture of G, A, C, and T at the position. A clone library of ~450 colonies were picked and evaluated for expression and efficacy in the brown stink bug diet bioassay. Variants showing improved properties in the stink bug bioassay were sequenced to determine the mutation.

Protein expression and insect bioassays: The protein was overexpressed in *E. coli* and purified according to the manufacturer's instructions using amylose resin. The eluted protein was evaluated by SDS-PAGE. The D18A and D75A variants showed a high molecular weight and SDS-resistant species in the SDS-PAGE experiment. The purified proteins were then incorporated into the diet bioassay and fed to brown stink bug nymphs at a high dose (1000 PPM). All of the single mutant variants showed activity on the brown stink bug (Table 8). Because of the unexpected high molecular weight complexes displayed in the D18 and D75 mutants, those positions were selected for further mutagenesis in a combinatorial site saturation library. Approximately 450 clones were selected from the D18/D75 library for evaluation in brown stink bug bioassay. Variants that performed well in the bioassay were sequenced (Table 8). These results indicated that the IRDIG37126 protein of SEQ ID NO:2 and SEQ ID NO:13-24 provided significant levels of mortality against BSB. For the first time, the IRDIG37126 protein variant sequences were shown to confer insecticidal activity by controlling or killing insect pests that ingested the IRDIG37126 protein variants.

TABLE 8

Activity of IRDIG37126 variant sequences against brown stink bug pests in the diet based bioassay.

| Variant Sequence | % Mortality | Insect Resistance Activity |
| --- | --- | --- |
| IRDIG37126_D6A (SEQ ID NO: 13) | 89 | Active |
| IRDIG37126_D18A (SEQ ID NO: 15) | 66 | Active |
| IRDIG37126_D18S (SEQ ID NO: 17) | 100 | Active |
| IRDIG37126_D18P (SEQ ID NO: 16) | 100 | Active |
| IRDIG37126_G23E (SEQ ID NO: 18) | 58 | Active |
| IRDIG37126_R28K (SEQ ID NO: 19) | 42 | Active |
| IRDIG37126_R28M (SEQ ID NO: 20) | 51 | Active |
| IRDIG37126_H13A (SEQ ID NO: 14) | 53 | Active |
| IRDIG37126_D75A (SEQ ID NO: 21) | 61 | Active |
| IRDIG37126_D18R_D75E (SEQ ID NO: 22) | 97 | Active |
| IRDIG37126_D18L_D75E (SEQ ID NO: 23) | 94 | Active |
| IRDIG37126_D18Q_D75E (SEQ ID NO: 24) | 100 | Active |
| Negative Control (water) | 18 | Inactive |
| IRDIG37126 Wild Type | 92 | Active |

Example 10: Identification of a Signature Protein Motif in the IRDIG37126 Protein The N-terminal region of IRDIG37126 is divergent from previously analyzed hemipteran active sequences (FIG. 7). This region of the protein may be involved in toxin maturation and the sequence was analyzed for motifs specific to IRDIG37126. Residues 19 through 25, "QLHVGEV" (SEQ ID NO:37), form a motif indicative of IRDIG37126, not found in previously described hemipteran active monalysins.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

---

That which is claimed:

1. A DNA construct comprising one or more heterologous regulatory sequences directing expression of a recombinant nucleic acid molecule encoding a polypeptide that has at least 98% sequence identity with SEQ ID NO:2, wherein the polypeptide has insecticidal activity.

2. The DNA construct of claim 1, wherein the polypeptide further comprises a signal sequence or a leader sequence.

3. The DNA construct of claim 1, further comprising a nucleic acid sequence encoding an additional transgenic trait.

4. The DNA construct of claim 3, wherein the one or more additional transgenic trait is selected from the group consisting of insect resistance, herbicide tolerance, nitrogen use efficiency, small RNA expression, site specific nuclease, water use efficiency, and nutritional quality.

5. An isolated polypeptide encoded by the DNA construct of claim 2.

6. A composition comprising an insecticidally-effective amount of the polypeptide of claim 5.

7. The composition of claim 6, further comprising one or more pesticidal proteins selected from the group consisting of a Cry1 protein, a Cry2 protein, a Cry3 protein, a Cry4 protein, a CryS5 protein, a Cry6 protein, a Cry7 protein, a Cry8 protein, a Cry9 protein, a Cry15 protein, Cry22 protein, a Cry23 protein, a Cry32 protein, a Cry34 protein, a Cry35 protein, a Cry36 protein, a Cry37 protein, a Cry43 protein, a Cry46 protein, a Cry51 protein, a Cry55 protein, a Cry binary toxin, a Cyt protein, a VIP toxin, a SIP protein, an insecticidal lipase, an insecticidal chitinase, and a snake venom protein.

8. The composition of claim 6, further comprising one or more pesticidal small RNA molecules.

9. The DNA construct of claim 1, wherein the polypeptide is orally active.

10. The DNA construct of claim 1, wherein the polypeptide has insecticidal activity against an insect pest in the order Hemiptera.

11. The DNA construct of claim 1, wherein the polypeptide has insecticidal activity against an insect pest in the family Pentatomidae.

12. The DNA construct of claim 1, wherein the polypeptide comprises any one or more amino acid modification relative to position 6 of SEQ ID NO:2, position 13 of SEQ ID NO:2, position 18 of SEQ ID NO:2, position 23 of SEQ ID NO:2, position 28 of SEQ ID NO:2, and/or position 75 of SEQ ID NO:2.

13. A method for controlling an insect pest population, the method comprising contacting the insect pest population with an insecticidally-effective amount of the polypeptide of claim 5.

14. A method of inhibiting growth or killing an insect pest, the method comprising contacting the insect pest with an insecticidally-effective amount of the polypeptide of claim 5.

15. A method for controlling an insect pest population resistant to a pesticidal protein, the method comprising contacting the insect pest population with an insecticidally-effective amount of the recombinant polypeptide of claim 5.

16. The DNA construct of claim 1, wherein the protein comprises the protein motif sequence of SEQ ID NO:37.

* * * * *

SEQUENCE LISTING

```
<160> NUMBER OF SEQ ID NOS: 37

<210> SEQ ID NO 1
<211> LENGTH: 813
<212> TYPE: DNA
<213> ORGANISM: Artificial Sequence
<220> FEATURE:
<223> OTHER INFORMATION: DNA coding sequence of IRDIG37126 (from an
      unknown bacterial strain)

<400> SEQUENCE: 1
atgacgatca aggaagactt gagcaatcct caaagccatt cggtcgagct cgaccagttg      60
cacgtcgggg aagtctctgc acgcgaagcg ttgaccgcca acttcgccgg cagtttcgat     120
cagttcccga ccaaaagcgg cagcttcgag atcgacaaat acctgctcaa ctacgcagac     180
ccgaaacaag gctgctggct ggacggcgtc accgtctacg gtgacatcta catcggcaag     240
cagaactggg gcacctacac gcgcccggtg ttcgcctacc tgcagcacac ggacaccatc     300
tcgattccgc agcaggtgac gcagaccaag agctaccagt tgagcaaagg ccacacccag     360
tcgttcacca agtcggtcag cgccaagtac agcgttggcg gcagtatcga catcgtcaac     420
gtcagctcgg atatcactgt cggtttcagc agcaccgagg cctggtcgac gacccagacc     480
ttcacccaaa gcaccgagct ggccggtccg ggcaccttct ttgtctatca ggtggtgttt     540
gtctacgcgc acaacgccac ctcggcgggc cggcagaatg gcaatgcctt tgcctatagc     600
aagacccagc aggtggattc gcggctcgat ctctactacc tgtcggccat cacccaggac     660
cgtacggtca tcgtcgagtc cagcaaggca atcaacccgc tggactggga taccgtgcag     720
cgcaacgtgc tgatcgagaa ctacaacccg gcctccaaca gtgggcactt ccgcttcgac     780
tggagcgcct acaacgatcc tcatcgccgc tac                                  813

<210> SEQ ID NO 2
<211> LENGTH: 271
<212> TYPE: PRT
<213> ORGANISM: Artificial Sequence
<220> FEATURE:
<223> OTHER INFORMATION: Protein sequence of IRDIG37126 (from an unknown
      bacterial strain)

<400> SEQUENCE: 2

Met Thr Ile Lys Glu Asp Leu Ser Asn Pro Gln Ser His Ser Val Glu
1               5                   10                  15

Leu Asp Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
```

```
                65                  70                  75                  80
Gln Asn Trp Gly Thr Tyr Thr Arg Pro Val Phe Ala Tyr Leu Gln His
                    85                  90                  95

Thr Asp Thr Ile Ser Ile Pro Gln Gln Val Thr Gln Thr Lys Ser Tyr
                100                 105                 110

Gln Leu Ser Lys Gly His Thr Gln Ser Phe Thr Lys Ser Val Ser Ala
                115                 120                 125

Lys Tyr Ser Val Gly Gly Ser Ile Asp Ile Val Asn Val Ser Ser Asp
130                 135                 140

Ile Thr Val Gly Phe Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
                180                 185                 190

Asn Gly Asn Ala Phe Ala Tyr Ser Lys Thr Gln Gln Val Asp Ser Arg
                195                 200                 205

Leu Asp Leu Tyr Tyr Leu Ser Ala Ile Thr Gln Asp Arg Thr Val Ile
                210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
                260                 265                 270

<210> SEQ ID NO 3
<211> LENGTH: 271
<212> TYPE: PRT
<213> ORGANISM: Pseudomonas

<400> SEQUENCE: 3

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
                20                  25                  30

Ser Asn Phe Ala Gly Asn Phe Asp Gln Phe Pro Thr Lys Arg Gly Gly
            35                  40                  45

Phe Ala Ile Asp Ser Tyr Leu Leu Asp Tyr Ser Ala Pro Lys Gln Gly
        50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
                100                 105                 110

Gln Leu Thr Lys Gly His Thr Lys Thr Phe Thr Thr Asn Val Ser Ala
                115                 120                 125

Lys Tyr Ser Val Gly Gly Ser Ile Asp Ile Val Asn Val Gly Ser Asp
130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175
```

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
        210                 215                 220

Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 4
<211> LENGTH: 271
<212> TYPE: PRT
<213> ORGANISM: Pseudomonas entomophila

<400> SEQUENCE: 4

Met Thr Ile Lys Glu Glu Leu Gly Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Leu Ser Gly Arg Phe Asp Gln Tyr Pro Thr Lys Lys Gly Asp
            35                  40                  45

Phe Ala Ile Asp Gly Tyr Leu Leu Asp Tyr Ser Ser Pro Lys Gln Gly
        50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
        130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
        210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
        260                 265                 270

<210> SEQ ID NO 5

<211> LENGTH: 271
<212> TYPE: PRT
<213> ORGANISM: Pseudomonas

<400> SEQUENCE: 5

Met Thr Ile Lys Glu Glu Leu Asn Gln Pro Gln Ser His Ser Ile Glu
1               5                   10                  15

Leu Asp Asp Leu Asn Ser Glu Gln Gly Asn Ala Arg Ala Ile Leu Thr
            20                  25                  30

Ser Asn Phe Ala Gly Ser Phe Asp Gln Phe Pro Thr Lys Arg Gly Gly
        35                  40                  45

Tyr Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Ser Val Thr Ala
        115                 120                 125

Lys Tyr Ser Val Gly Gly Ser Ile Gly Ile Val Asn Val Gly Ser Asp
    130                 135                 140

Ile Ser Val Gly Phe Ser Ser Glu Ser Trp Ser Thr Thr Gln Thr
145                 150                 155                 160

Phe Ser Glu Ser Thr Gln Leu Ala Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Gln Thr Val Gly Ser Arg
        195                 200                 205

Leu Asp Leu Tyr Tyr Leu Ser Ala Ile Thr Gln Asn Ser Thr Val Ile
    210                 215                 220

Val Glu Ser Ser Lys Ala Ile Ala Pro Leu Asp Trp Asp Thr Val Gln
225                 230                 235                 240

Arg Asn Val Leu Met Glu Asn Tyr Asn Pro Ser Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 6
<211> LENGTH: 271
<212> TYPE: PRT
<213> ORGANISM: Pseudomonas

<400> SEQUENCE: 6

Met Thr Ile Lys Glu Glu Leu Asn Gln Pro Gln Ser His Ser Ile Glu
1               5                   10                  15

Leu Asp Asp Leu Asn Ser Glu Gln Gly Asn Ala Arg Ala Ile Leu Thr
            20                  25                  30

Ser Asn Phe Ala Gly Asn Phe Asp Gln Phe Pro Thr Lys Arg Gly Gly
        35                  40                  45

Tyr Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

```
Gln Asn Trp Gly Thr Tyr Thr Arg Pro Val Phe Ala Tyr Leu Gln Tyr
             85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Ser Val Thr Ala
            115                 120                 125

Lys Tyr Ser Val Gly Gly Ser Ile Gly Ile Val Asn Val Gly Ser Asp
    130                 135                 140

Ile Ser Val Gly Phe Ser Ser Glu Ser Trp Ser Thr Thr Gln Thr
145                 150                 155                 160

Phe Ser Glu Ser Thr Gln Leu Thr Gly Pro Gly Thr Phe Ile Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Gln Thr Val Gly Ser Arg
        195                 200                 205

Leu Asp Leu Tyr Tyr Leu Ser Ala Ile Thr Gln Asn Ser Thr Val Ile
    210                 215                 220

Val Glu Ser Ser Lys Ala Ile Ala Pro Leu Asp Trp Asp Thr Val Gln
225                 230                 235                 240

Arg Asn Val Leu Met Glu Asn Tyr Asn Pro Ser Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 7
<211> LENGTH: 271
<212> TYPE: PRT
<213> ORGANISM: Pseudomonas

<400> SEQUENCE: 7

Met Thr Ile Lys Glu Glu Leu Asn Gln Pro Gln Ser His Ser Ile Glu
1               5                   10                  15

Leu Asp Asp Leu Asn Ser Glu Gln Gly Asn Ala Arg Ala Ile Leu Thr
            20                  25                  30

Ser Asn Phe Ala Gly Ser Phe Asp Gln Phe Pro Thr Lys Arg Gly Gly
        35                  40                  45

Tyr Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
             85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Ser Val Thr Ala
            115                 120                 125

Lys Tyr Ser Val Gly Gly Ser Ile Gly Ile Val Asn Val Gly Ser Asp
    130                 135                 140

Ile Ser Val Gly Phe Ser Ser Glu Ser Trp Ser Thr Thr Gln Thr
145                 150                 155                 160

Phe Ser Glu Ser Thr Gln Leu Thr Gly Pro Gly Thr Phe Ile Val Tyr
                165                 170                 175

Gln Val Val Leu Val Tyr Ala His Asn Ala Thr Ser Ala Gly Arg Gln
```

```
                180                 185                 190
Asn Gly Asn Ala Phe Ala Tyr Asn Lys Thr Gln Thr Val Gly Ser Arg
            195                 200                 205

Leu Asp Leu Tyr Tyr Leu Ser Ala Ile Thr Gln Asn Ser Thr Val Ile
        210                 215                 220

Val Glu Ser Ser Lys Ala Ile Ala Pro Leu Asp Trp Asp Thr Val Gln
225                 230                 235                 240

Arg Asn Val Leu Met Glu Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 8
<211> LENGTH: 273
<212> TYPE: PRT
<213> ORGANISM: Pseudomonas

<400> SEQUENCE: 8

```
Met Thr Ile Lys Glu Glu Leu Ser Leu Pro Gln Ser His Ser Ile Asp
1               5                   10                  15

Val Asp Glu Leu Lys Gln Glu His Glu His Gly Ser Ala Arg Ala Val
            20                  25                  30

Leu Thr Ser Asn Phe Ser Gly Ser Phe Asp Gln Phe Pro Thr Lys Arg
        35                  40                  45

Gly Gly Phe Ala Ile Asp Ser Tyr Leu Leu Asp Tyr Ser Ala Pro Lys
    50                  55                  60

Gln Gly Cys Trp Val Asp Gly Ile Thr Val Tyr Gly Asp Ile Tyr Ile
65                  70                  75                  80

Gly Lys Gln Asn Trp Gly Thr Tyr Thr Arg Pro Val Phe Ala Tyr Leu
                85                  90                  95

Gln Tyr Met Asp Thr Ile Ser Ile Pro Gln Gln Val Thr Gln Thr Arg
            100                 105                 110

Ser Tyr Gln Leu Thr Lys Gly His Thr Lys Thr Phe Thr Thr Ser Val
        115                 120                 125

Asn Ala Lys Tyr Ser Val Gly Gly Ser Ile Gly Ile Val Asn Val Gly
    130                 135                 140

Ser Glu Ile Ser Val Gly Phe Ser Ser Ser Glu Ser Trp Ser Thr Thr
145                 150                 155                 160

Gln Thr Phe Thr Glu Ser Thr Gln Leu Thr Gly Pro Gly Thr Phe Ile
                165                 170                 175

Val Tyr Gln Val Val Leu Val Tyr Ala His Asn Ala Thr Ser Ala Gly
            180                 185                 190

Arg Gln Asn Gly Asn Val Phe Ala Tyr Asn Lys Thr Ser Thr Val Gly
        195                 200                 205

Ser Arg Leu Asp Leu Tyr Tyr Leu Ser Ala Ile Thr Gln Asn Ser Thr
    210                 215                 220

Val Ile Val Glu Ser Ser Lys Ala Ile Ala Pro Leu Asp Trp Asp Thr
225                 230                 235                 240

Val Gln Arg Asn Val Leu Met Glu Asn Tyr Asn Pro Ala Ser Asn Ser
                245                 250                 255

Gly His Phe Arg Phe Asp Trp Ser Ala Tyr Asp Asp Pro His Arg Arg
            260                 265                 270

Tyr
```

<210> SEQ ID NO 9
<211> LENGTH: 271
<212> TYPE: PRT
<213> ORGANISM: Pseudomonas

<400> SEQUENCE: 9

Met Thr Ile Lys Glu Glu Leu Gly Gln Pro Gln Ser His Ser Ile Glu
1               5                   10                  15

Leu Asp Cys Leu Asn Arg Glu Ala Gly Ser Ala Arg Ala Ala Leu Thr
            20                  25                  30

Ser Asn Leu Val Gly Ser Phe Asp Gln Tyr Pro Thr Lys His Gly Asp
        35                  40                  45

Phe Ala Ile Asp Ser Tyr Leu Leu Asp Phe Ser Ala Pro Lys Lys Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Ile Gln Thr Arg Ser Tyr
            100                 105                 110

Gln Leu Thr Lys Gly His Thr Gln Thr Phe Glu Thr Val Ser Ala
        115                 120                 125

Lys Tyr Ser Val Gly Ala Lys Ile Asp Ile Val Asn Ile Asp Ser Glu
130                 135                 140

Ile Ser Thr Gly Phe Ser Ser Glu Ser Trp Ser Thr Thr Gln Thr
145                 150                 155                 160

Phe Ser Glu Ser Thr Gln Leu Ser Gly Pro Gly Thr Phe Met Val Tyr
                165                 170                 175

Gln Ile Val Leu Val Tyr Ala His Asn Ala Thr Ser Ala Gly Lys Gln
            180                 185                 190

Asn Gly Asn Ala Phe Ala Tyr Ser Lys Thr Gln Thr Val Asp Ser Arg
        195                 200                 205

Val Asp Leu Tyr Tyr Leu Ser Ala Ile Thr Gln Asn Lys Thr Val Ile
    210                 215                 220

Val Gln Ser Gly Asn Ala Ile Glu Pro Leu Asp Trp Asp Thr Val Gln
225                 230                 235                 240

Arg Asn Val Leu Met Asp Asn Tyr Asn Pro Glu Ser Asn Asn Gly His
                245                 250                 255

Phe Arg Phe Asp Trp Ser Ala Tyr Asp Asn Pro His Arg Arg Tyr
            260                 265                 270

<210> SEQ ID NO 10
<211> LENGTH: 271
<212> TYPE: PRT
<213> ORGANISM: Pseudomonas

<400> SEQUENCE: 10

Met Thr Ile Lys Glu Glu Leu Gly Gln Pro Gln Ser His Ser Ile Glu
1               5                   10                  15

Leu Asp Ser Leu Ser Gly Glu Ala Gly Asp Ile Arg Ala Ala Leu Thr
            20                  25                  30

Ser Asn Leu Ala Gly Ser Phe Asp Gln Tyr Pro Thr Lys Ser Gly Asp
        35                  40                  45

Phe Gln Ile Asp Ser Tyr Leu Leu Asp Tyr Ser Ala Pro Lys Gln Gly
    50                  55                  60

Cys Trp Val Asn Gly Ile Thr Val Tyr Gly Asp Ile Tyr Ile Gly Lys

-continued

```
                65                  70                  75                  80
Gln Asn Trp Gly Thr Tyr Thr Arg Pro Val Phe Ala Tyr Leu Gln Tyr
                    85                  90                  95

Met Asp Thr Ile Ser Ile Pro Gln Gln Val Thr Gln Thr Arg Ser Tyr
                    100                 105                 110

Gln Leu Thr Lys Gly His Thr Gln Ser Phe Thr Thr Ser Val Ser Ala
                    115                 120                 125

Lys Tyr Ser Val Gly Ala Lys Ile Asp Ile Val Asn Ile Gly Ser Glu
                    130                 135                 140

Ile Ser Thr Gly Phe Ser Gln Thr Glu Ser Trp Ser Thr Thr Gln Thr
145                 150                 155                 160

Phe Thr Glu Ser Thr Gln Leu Thr Gly Pro Gly Thr Phe Met Val Tyr
                    165                 170                 175

Gln Ile Val Met Val Tyr Ala His Asn Ala Thr Ser Ala Gly Arg Gln
                    180                 185                 190

Asn Ser Asn Ala Phe Ala Tyr Ser Lys Thr Gln Asp Val Gly Ser Arg
                    195                 200                 205

Val Asp Leu Tyr Tyr Leu Ser Ala Ile Thr Leu Asp Lys Lys Val Ile
                    210                 215                 220

Val Gln Ser Gly Gln Ala Ile Ser Pro Leu Asp Trp Asn Thr Val Gln
225                 230                 235                 240

Arg Asn Val Leu Met Glu Asn Tyr Asn Thr Gly Ser Asn Asn Gly His
                    245                 250                 255

Phe Ser Phe Asp Trp Ser Ala Tyr Asn Asp Pro His Arg Arg Tyr
                    260                 265                 270
```

<210> SEQ ID NO 11
<211> LENGTH: 264
<212> TYPE: PRT
<213> ORGANISM: Cystobacter

<400> SEQUENCE: 11

```
Met Asn Val Thr Gln Gln Asp Ala Gly Leu Leu Glu Leu Arg Asn Val
1               5                   10                  15

Ser Asp Phe Leu Arg His Gln Lys Ser Ala Val Thr Ala Pro Asn Ile
                    20                  25                  30

Val Thr Gly Gln Leu Asn Ser Thr Ser Tyr Pro Trp Ala Val Gly Gly
                    35                  40                  45

Asp Ser Gly Ile Asp Ser Cys Leu Lys Asn Glu Asp Pro Pro Gly
            50                  55                  60

Cys Trp Val Asp Gly Glu Thr Val His Gly Ile Tyr Ile Lys Thr
65                  70                  75                  80

Gln Ser Trp Gly Thr Tyr Thr Arg Pro Ile Phe Ala Tyr Leu Lys Tyr
                    85                  90                  95

Val Ser Thr Tyr Thr Tyr Pro Ser Gly Ala Ser Gln His Tyr Thr Thr
                    100                 105                 110

Thr Gln Thr Val Gly Leu Thr Glu Thr Phe Thr Lys Glu Val Lys Ala
                    115                 120                 125

Ser Tyr Ser Val Gly Ala Asn Ile Asp Ile Val Asn Thr Ser Ser Ser
                    130                 135                 140

Ile Glu Thr Gly Phe Ser Arg Ala Ser Ser Trp Ser Gln Gln Thr Ile
145                 150                 155                 160

Gln Ser Trp Thr Thr Lys Leu Gln Gly Pro Ala Thr Phe Tyr Ile Tyr
                    165                 170                 175
```

```
Gln Val Ala Leu Val Tyr Ala His Cys Ala Thr Met Ala Gly Lys Ser
            180                 185                 190

Cys Ala Ser Ser Phe Lys Tyr Gln Arg Thr Arg Val Ile Asn Asp Gly
        195                 200                 205

Arg Thr Asp Leu Tyr Tyr Leu Ser Ser Ile Ser Lys Lys Asp Met Val
    210                 215                 220

Ile Leu Ser Lys Pro Leu Ile Pro Leu Ser Trp Asp Gln Val Gln Gln
225                 230                 235                 240

Tyr Val Leu Ile Asp Asn Trp Asn Thr Trp Tyr Phe Asp Tyr Ser Ala
                245                 250                 255

Tyr Ser Asp Pro Phe Arg Arg Tyr
            260

<210> SEQ ID NO 12
<211> LENGTH: 270
<212> TYPE: PRT
<213> ORGANISM: Cystobacter

<400> SEQUENCE: 12

Met Ile Asn Glu Lys Ser Val Asn Val Ala Lys Gln Asp Ala Gly Pro
1               5                   10                  15

Leu Glu Leu Lys Asn Val Ser Asp Phe Leu Arg His Gln Lys Ser Ala
            20                  25                  30

Val Ala Ala Pro Asn Ile Val Thr Gly Gln Leu Asn Ser Thr Ser His
        35                  40                  45

Pro Trp Ala Met Gly Gly Asn Phe Gly Ile Asp Gln Cys Leu Lys Asn
    50                  55                  60

Gln Asp Pro Pro Gly Cys Trp Val Asp Gly Glu Thr Val His Gly
65                  70                  75                  80

Asp Ile Tyr Ile Lys Thr Gln Asn Trp Gly Thr Tyr Thr Arg Pro Ile
                85                  90                  95

Phe Ala Tyr Leu Lys Tyr Val Asn Thr Tyr Thr Tyr Pro Ser Gly Ala
            100                 105                 110

Ser Gln Gln Tyr Thr Thr Thr Gln Thr Val Gly Leu Thr Glu Thr Phe
        115                 120                 125

Thr Thr Glu Val Lys Ala Ser Tyr Ser Val Gly Ala Asn Ile Asp Ile
    130                 135                 140

Val Asn Val Gly Ser Ser Ile Glu Thr Gly Phe Ser Lys Ser Ser Ser
145                 150                 155                 160

Trp Ser Gln Gln Thr Thr Gln Ser Trp Thr Thr Thr Leu Gln Gly Pro
                165                 170                 175

Ala Thr Phe Tyr Ile Tyr Gln Val Ala Leu Val Tyr Ala His Cys Ala
            180                 185                 190

Thr Thr Ala Gly Lys Ser Cys Ala Ser Ser Phe Lys Tyr Gln Arg Thr
        195                 200                 205

Arg Val Ile Asn Asp Trp Arg Thr Asp Leu Tyr Tyr Leu Ser Ala Ile
    210                 215                 220

Ser Lys Asn Asp Met Val Ile Leu Ser Lys Pro Leu Ile Pro Leu Ser
225                 230                 235                 240

Trp Glu Gln Val Gln Gln Tyr Val Leu Ile Asp Asn Trp Asn Thr Trp
                245                 250                 255

Tyr Phe Asp Tyr Ser Ala Tyr Ser Asp Pro Phe Arg Arg Tyr
            260                 265                 270

<210> SEQ ID NO 13
```

<211> LENGTH: 271
<212> TYPE: PRT
<213> ORGANISM: artificial sequence
<220> FEATURE:
<223> OTHER INFORMATION: >IRDIG37126_D6A (protein sequence)

<400> SEQUENCE: 13

Met Thr Ile Lys Glu Ala Leu Ser Asn Pro Gln Ser His Ser Val Glu
1               5                   10                  15

Leu Asp Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 14
<211> LENGTH: 271
<212> TYPE: PRT
<213> ORGANISM: artificial sequence
<220> FEATURE:
<223> OTHER INFORMATION: >IRDIG37126_H13A (protein sequence)

<400> SEQUENCE: 14

Met Thr Ile Lys Glu Asp Leu Ser Asn Pro Gln Ser Ala Ser Val Glu
1               5                   10                  15

Leu Asp Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
            165                 170                 175

Gln Val Val Phe Val Tyr Ala His Asn Ala Thr Ser Ala Gly Arg Gln
        180                 185                 190

Asn Gly Asn Ala Phe Ala Tyr Ser Lys Thr Gln Gln Val Asp Ser Arg
    195                 200                 205

Leu Asp Leu Tyr Tyr Leu Ser Ala Ile Thr Gln Asp Arg Thr Val Ile
        210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
            245                 250                 255

Phe Arg Phe Asp Trp Ser Ala Tyr Asn Asp Pro His Arg Arg Tyr
            260                 265                 270

<210> SEQ ID NO 15
<211> LENGTH: 271
<212> TYPE: PRT
<213> ORGANISM: artificial sequence
<220> FEATURE:
<223> OTHER INFORMATION: >IRDIG37126_D18A (protein sequence)

<400> SEQUENCE: 15

Met Thr Ile Lys Glu Asp Leu Ser Asn Pro Gln Ser His Ser Val Glu
1               5                   10                  15

Leu Ala Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr

```
145                 150                 155                 160
Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
                180                 185                 190

Asn Gly Asn Ala Phe Ala Tyr Ser Lys Thr Gln Gln Val Asp Ser Arg
                195                 200                 205

Leu Asp Leu Tyr Tyr Leu Ser Ala Ile Thr Gln Asp Arg Thr Val Ile
                210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
                260                 265                 270

<210> SEQ ID NO 16
<211> LENGTH: 271
<212> TYPE: PRT
<213> ORGANISM: artificial sequence
<220> FEATURE:
<223> OTHER INFORMATION: >IRDIG37126_D18P (protein sequence)

<400> SEQUENCE: 16

Met Thr Ile Lys Glu Asp Leu Ser Asn Pro Gln Ser His Ser Val Glu
1               5                   10                  15

Leu Pro Gln Leu His Val Gly Glu Val Ser Ala Arg Glu Ala Leu Thr
                20                  25                  30

Ala Asn Phe Ala Gly Ser Phe Asp Gln Phe Pro Thr Lys Ser Gly Ser
                35                  40                  45

Phe Glu Ile Asp Lys Tyr Leu Leu Asn Tyr Ala Asp Pro Lys Gln Gly
50                  55                  60

Cys Trp Leu Asp Gly Val Thr Val Tyr Gly Ser Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
                100                 105                 110

Gln Leu Ser Lys Gly His Thr Gln Ser Phe Thr Lys Ser Val Ser Ala
                115                 120                 125

Lys Tyr Ser Val Gly Gly Ser Ile Asp Ile Val Asn Val Ser Ser Asp
                130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
                180                 185                 190

Asn Gly Asn Ala Phe Ala Tyr Ser Lys Thr Gln Gln Val Asp Ser Arg
                195                 200                 205

Leu Asp Leu Tyr Tyr Leu Ser Ala Ile Thr Gln Asp Arg Thr Val Ile
                210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
```

```
                        245                 250                 255

Phe Arg Phe Asp Trp Ser Ala Tyr Asn Asp Pro His Arg Arg Tyr
            260                 265                 270

<210> SEQ ID NO 17
<211> LENGTH: 271
<212> TYPE: PRT
<213> ORGANISM: artificial sequence
<220> FEATURE:
<223> OTHER INFORMATION: >IRDIG37126_D18S (protein sequence)

<400> SEQUENCE: 17

Met Thr Ile Lys Glu Asp Leu Ser Asn Pro Gln Ser His Ser Val Glu
1               5                   10                  15

Leu Ser Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 18
<211> LENGTH: 271
<212> TYPE: PRT
<213> ORGANISM: artificial sequence
<220> FEATURE:
<223> OTHER INFORMATION: >IRDIG37126_G23E (protein sequence)

<400> SEQUENCE: 18

Met Thr Ile Lys Glu Asp Leu Ser Asn Pro Gln Ser His Ser Val Glu
1               5                   10                  15
```

Leu Asp Gln Leu His Val Glu Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 19
<211> LENGTH: 271
<212> TYPE: PRT
<213> ORGANISM: artificial sequence
<220> FEATURE:
<223> OTHER INFORMATION: >IRDIG37126_R28K (protein sequence)

<400> SEQUENCE: 19

Met Thr Ile Lys Glu Asp Leu Ser Asn Pro Gln Ser His Ser Val Glu
1               5                   10                  15

Leu Asp Gln Leu His Val Gly Glu Val Ser Ala Lys Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

```
Gln Leu Ser Lys Gly His Thr Gln Ser Phe Thr Lys Ser Val Ser Ala
            115                 120                 125

Lys Tyr Ser Val Gly Gly Ser Ile Asp Ile Val Asn Val Ser Ser Asp
        130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270
```

<210> SEQ ID NO 20
<211> LENGTH: 271
<212> TYPE: PRT
<213> ORGANISM: artificial sequence
<220> FEATURE:
<223> OTHER INFORMATION: >IRDIG37126_R28M (protein sequence)

<400> SEQUENCE: 20

```
Met Thr Ile Lys Glu Asp Leu Ser Asn Pro Gln Ser His Ser Val Glu
1               5                   10                  15

Leu Asp Gln Leu His Val Gly Glu Val Ser Ala Met Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205
```

```
Leu Asp Leu Tyr Tyr Leu Ser Ala Ile Thr Gln Asp Arg Thr Val Ile
        210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270
```

<210> SEQ ID NO 21
<211> LENGTH: 271
<212> TYPE: PRT
<213> ORGANISM: artificial sequence
<220> FEATURE:
<223> OTHER INFORMATION: >IRDIG37126_D75A (protein sequence)

<400> SEQUENCE: 21

```
Met Thr Ile Lys Glu Asp Leu Ser Asn Pro Gln Ser His Ser Val Glu
1               5                   10                  15

Leu Asp Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
50                  55                  60

Cys Trp Leu Asp Gly Val Thr Val Tyr Gly Ala Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270
```

<210> SEQ ID NO 22
<211> LENGTH: 271
<212> TYPE: PRT
<213> ORGANISM: artificial sequence
<220> FEATURE:

<223> OTHER INFORMATION: >IRDIG37126_D18R_D75E (protein sequence)

<400> SEQUENCE: 22

```
Met Thr Ile Lys Glu Asp Leu Ser Asn Pro Gln Ser His Ser Val Glu
1               5                   10                  15

Leu Arg Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Glu Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Val Ser Ser Asp
130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270
```

<210> SEQ ID NO 23
<211> LENGTH: 271
<212> TYPE: PRT
<213> ORGANISM: artificial sequence
<220> FEATURE:
<223> OTHER INFORMATION: >IRDIG37126_D18L_D75E (protein sequence)

<400> SEQUENCE: 23

```
Met Thr Ile Lys Glu Asp Leu Ser Asn Pro Gln Ser His Ser Val Glu
1               5                   10                  15

Leu Leu Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Glu Ile Tyr Ile Gly Lys
65                  70                  75                  80
```

Gln Asn Trp Gly Thr Tyr Thr Arg Pro Val Phe Ala Tyr Leu Gln His
            85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
            115                 120                 125

Lys Tyr Ser Val Gly Gly Ser Ile Asp Ile Val Asn Val Ser Ser Asp
            130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
            165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
            195                 200                 205

Leu Asp Leu Tyr Tyr Leu Ser Ala Ile Thr Gln Asp Arg Thr Val Ile
            210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
            245                 250                 255

Phe Arg Phe Asp Trp Ser Ala Tyr Asn Asp Pro His Arg Arg Tyr
            260                 265                 270

```
<210> SEQ ID NO 24
<211> LENGTH: 271
<212> TYPE: PRT
<213> ORGANISM: artificial sequence
<220> FEATURE:
<223> OTHER INFORMATION: >IRDIG37126_D18Q_D75E (protein sequence)

<400> SEQUENCE: 24
```

Met Thr Ile Lys Glu Asp Leu Ser Asn Pro Gln Ser His Ser Val Glu
1               5                   10                  15

Leu Gln Gln Leu His Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
            35                  40                  45

Phe Glu Ile Asp Lys Tyr Leu Leu Asn Tyr Ala Asp Pro Lys Gln Gly
            50                  55                  60

Cys Trp Leu Asp Gly Val Thr Val Tyr Gly Glu Ile Tyr Ile Gly Lys
65                  70                  75                  80

Gln Asn Trp Gly Thr Tyr Thr Arg Pro Val Phe Ala Tyr Leu Gln His
            85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
            115                 120                 125

Lys Tyr Ser Val Gly Gly Ser Ile Asp Ile Val Asn Val Ser Ser Asp
            130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
            165                 170                 175

```
Gln Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 25
<211> LENGTH: 813
<212> TYPE: DNA
<213> ORGANISM: artificial sequence
<220> FEATURE:
<223> OTHER INFORMATION: >IRDIG37126_D6A (nucleotide sequence)

<400> SEQUENCE: 25
atgacaatca aagaggccct gagcaaccct cagtcgcact ctgtggaatt agaccaactg      60
cacgtcggcg aggtatcagc ccgcgaagcc cttaccgcta acttcgccgg gtcctttgac     120
caatttccta caaaatctgg tagttttgag attgacaaat accttcttaa ttacgccgat     180
cccaaacaag ggtgttggtt agacggggta accgtctacg gtgacatcta catcggcaag     240
cagaactggg gcacctacac gcgcccggtg ttcgcctacc tgcagcacac ggacaccatc     300
tcgattccgc agcaggtgac gcagaccaag agctaccagt tgagcaaagg ccacacccag     360
tcgttcacca gtcggtcag cgccaagtac agcgttggcg cagtatcga catcgtcaac      420 gtcagctcgg atatcactgt cggtttcagc agcaccgagg cctggtcgac gacccagacc     480
ttcacccaaa gcaccgagct ggccggtccg ggcaccttct tgtctatca ggtggtgttt      540 gtctacgcgc acaacgccac ctcggcgggc cggcagaatg caatgccttt gcctatagc      600 aagacccagc aggtggattc gcggctcgat ctctactacc tgtcggccat cacccaggac     660
cgtacggtca tcgtcgagtc cagcaaggca atcaacccgc tggactggga taccgtgcag     720
cgcaacgtgc tgatcgagaa ctacaacccg gcctccaaca gtgggcactt ccgcttcgac     780
tggagcgcct acaacgatcc tcatcgccgc tac                                  813

<210> SEQ ID NO 26
<211> LENGTH: 813
<212> TYPE: DNA
<213> ORGANISM: artificial sequence
<220> FEATURE:
<223> OTHER INFORMATION: >IRDIG37126_H13A (nucleotide sequence)

<400> SEQUENCE: 26
atgacaatca aagaggatct gagcaaccct cagtcggcct ctgtggaatt agaccaactg      60
cacgtcggcg aggtatcagc ccgcgaagcc cttaccgcta acttcgccgg gtcctttgac     120
caatttccta caaaatctgg tagttttgag attgacaaat accttcttaa ttacgccgat     180
cccaaacaag ggtgttggtt agacggggta accgtctacg gtgacatcta catcggcaag     240
cagaactggg gcacctacac gcgcccggtg ttcgcctacc tgcagcacac ggacaccatc     300
tcgattccgc agcaggtgac gcagaccaag agctaccagt tgagcaaagg ccacacccag     360
```

```
tcgttcacca agtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct ttgtctatca ggtggtgttt    540
gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813
```

<210> SEQ ID NO 27
<211> LENGTH: 813
<212> TYPE: DNA
<213> ORGANISM: artificial sequence
<220> FEATURE:
<223> OTHER INFORMATION: >IRDIG37126_D18A (nucleotide sequence)

<400> SEQUENCE: 27

```
atgacaatca aagaggatct gagcaaccct cagtcgcact ctgtggaatt agcccaactg     60
cacgtcggcg aggtatcagc ccgcgaagcc cttaccgcta acttcgccgg gtcctttgac    120
caatttccta caaatctgg tagttttgag attgacaaat accttcttaa ttacgccgat     180
cccaaacaag ggtgttggtt agacggggta accgtctacg gtgacatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca agtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct ttgtctatca ggtggtgttt    540
gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813
```

<210> SEQ ID NO 28
<211> LENGTH: 813
<212> TYPE: DNA
<213> ORGANISM: artificial sequence
<220> FEATURE:
<223> OTHER INFORMATION: >IRDIG37126_D18P (nucleotide sequence)

<400> SEQUENCE: 28

```
atgacgatca aggaagactt gagcaatcct caaagccatt cggtcgagct cccgcagttg     60
cacgtcgggg aagtctctgc acgcgaagcg ttgaccgcca acttcgccgg cagtttcgat    120
cagttcccga ccaaaagcgg cagcttcgag atcgacaaat acctgctcaa ctacgcagac    180
ccgaaacaag gctgctggct ggacggcgtc accgtctacg gtgacatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca agtcggtcag cgccaagtac agcgttggcg gcagtatcga catcgtcaac    420
gtcagctcgg atatcactgt cggtttcagc agcaccgagg cctggtcgac gacccagacc    480
```

```
ttcacccaaa gcaccgagct ggccggtccg ggcaccttct ttgtctatca ggtggtgttt    540
gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813

<210> SEQ ID NO 29
<211> LENGTH: 813
<212> TYPE: DNA
<213> ORGANISM: artificial sequence
<220> FEATURE:
<223> OTHER INFORMATION: >IRDIG37126_G23E (nucleotide sequence)

<400> SEQUENCE: 29
atgacaatca agaggatct gagcaaccct cagtcgcact ctgtggaatt agaccaactg      60
cacgtcgagg aggtatcagc ccgcgaagcc cttaccgcta acttcgccgg gtcctttgac    120
caatttccta caaatctgg tagttttgag attgacaaat accttcttaa ttacgccgat    180
cccaaacaag ggtgttggtt agacggggta accgtctacg gtgacatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca gtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct ttgtctatca ggtggtgttt    540
gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813

<210> SEQ ID NO 30
<211> LENGTH: 813
<212> TYPE: DNA
<213> ORGANISM: artificial sequence
<220> FEATURE:
<223> OTHER INFORMATION: >IRDIG37126_R28K (nucleotide sequence)

<400> SEQUENCE: 30
atgacaatca agaggatct gagcaaccct cagtcgcact ctgtggaatt agaccaactg      60
cacgtcggcg aggtatcagc caaagaagcc cttaccgcta acttcgccgg gtcctttgac    120
caatttccta caaatctgg tagttttgag attgacaaat accttcttaa ttacgccgat    180
cccaaacaag ggtgttggtt agacggggta accgtctacg gtgacatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca gtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct ttgtctatca ggtggtgttt    540
```

| gtctacgcgc acaacgccac ctcggcgggc cggcagaatg gcaatgcctt tgcctatagc | 600 |
| aagacccagc aggtggattc gcggctcgat ctctactacc tgtcggccat cacccaggac | 660 |
| cgtacggtca tcgtcgagtc cagcaaggca atcaacccgc tggactggga taccgtgcag | 720 |
| cgcaacgtgc tgatcgagaa ctacaacccg gcctccaaca gtgggcactt ccgcttcgac | 780 |
| tggagcgcct acaacgatcc tcatcgccgc tac | 813 |

<210> SEQ ID NO 31
<211> LENGTH: 813
<212> TYPE: DNA
<213> ORGANISM: artificial sequence
<220> FEATURE:
<223> OTHER INFORMATION: >IRDIG37126_R28M (nucleotide sequence)

<400> SEQUENCE: 31

| atgacaatca aagaggatct gagcaaccct cagtcgcact ctgtggaatt agaccaactg | 60 |
| cacgtcggcg aggtatcagc catggaagcc cttaccgcta acttcgccgg gtcctttgac | 120 |
| caatttccta caaaatctgg tagttttgag attgacaaat accttcttaa ttacgccgat | 180 |
| cccaaacaag ggtgttggtt agacggggta accgtctacg gtgacatcta catcggcaag | 240 |
| cagaactggg gcacctacac gcgcccggtg ttcgcctacc tgcagcacac ggacaccatc | 300 |
| tcgattccgc agcaggtgac gcagaccaag agctaccagt tgagcaaagg ccacacccag | 360 |
| tcgttcacca gtcggtcag cgccaagtac agcgttggcg cagtatcga catcgtcaac | 420 |
| gtcagctcgg atatcactgt cggtttcagc agcaccgagg cctggtcgac gacccagacc | 480 |
| ttcacccaaa gcaccgagct ggccggtccg ggcaccttct tgtctatcg ggtggtgttt | 540 |
| gtctacgcgc acaacgccac ctcggcgggc cggcagaatg gcaatgcctt tgcctatagc | 600 |
| aagacccagc aggtggattc gcggctcgat ctctactacc tgtcggccat cacccaggac | 660 |
| cgtacggtca tcgtcgagtc cagcaaggca atcaacccgc tggactggga taccgtgcag | 720 |
| cgcaacgtgc tgatcgagaa ctacaacccg gcctccaaca gtgggcactt ccgcttcgac | 780 |
| tggagcgcct acaacgatcc tcatcgccgc tac | 813 |

<210> SEQ ID NO 32
<211> LENGTH: 813
<212> TYPE: DNA
<213> ORGANISM: artificial sequence
<220> FEATURE:
<223> OTHER INFORMATION: >IRDIG37126_D75A (nucleotide sequence)

<400> SEQUENCE: 32

| atgacgatca aggaagactt gagcaatcct caaagccatt cggtcgagct cgaccagttg | 60 |
| cacgtcgggg aagtctctgc acgcgaagcg ttgaccgcca acttcgccgg cagtttcgat | 120 |
| cagttcccga ccaaaagcgg cagcttcgag atcgacaaat acctgctcaa ctacgcagac | 180 |
| ccgaaacaag gctgctggct ggacggcgtc accgtctacg gtgcgatcta catcggcaag | 240 |
| cagaactggg gcacctacac gcgcccggtg ttcgcctacc tgcagcacac ggacaccatc | 300 |
| tcgattccgc agcaggtgac gcagaccaag agctaccagt tgagcaaagg ccacacccag | 360 |
| tcgttcacca gtcggtcag cgccaagtac agcgttggcg cagtatcga catcgtcaac | 420 |
| gtcagctcgg atatcactgt cggtttcagc agcaccgagg cctggtcgac gacccagacc | 480 |
| ttcacccaaa gcaccgagct ggccggtccg ggcaccttct tgtctatcg ggtggtgttt | 540 |
| gtctacgcgc acaacgccac ctcggcgggc cggcagaatg gcaatgcctt tgcctatagc | 600 |
| aagacccagc aggtggattc gcggctcgat ctctactacc tgtcggccat cacccaggac | 660 |

```
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813
```

```
<210> SEQ ID NO 33
<211> LENGTH: 813
<212> TYPE: DNA
<213> ORGANISM: artificial sequence
<220> FEATURE:
<223> OTHER INFORMATION: >IRDIG37126_D18R_D75E (nucleotide sequence)

<400> SEQUENCE: 33
atgacgatca aggaagactt gagcaatcct caaagccatt cggtcgagct ccggcagttg     60
cacgtcgggg aagtctctgc acgcgaagcg ttgaccgcca acttcgccgg cagtttcgat    120
cagttcccga ccaaaagcgg cagcttcgag atcgacaaat acctgctcaa ctacgcagac    180
ccgaaacaag gctgctggct ggacggcgtc accgtctacg gtgaaatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca gtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct tgtctatca ggtggtgttt    540 gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgccgc tac                                 813
```

```
<210> SEQ ID NO 34
<211> LENGTH: 813
<212> TYPE: DNA
<213> ORGANISM: artificial sequence
<220> FEATURE:
<223> OTHER INFORMATION: >IRDIG37126_D18S_D75E (nucleotide sequence)

<400> SEQUENCE: 34
atgacgatca aggaagactt gagcaatcct caaagccatt cggtcgagct cagccagttg     60
cacgtcgggg aagtctctgc acgcgaagcg ttgaccgcca acttcgccgg cagtttcgat    120
cagttcccga ccaaaagcgg cagcttcgag atcgacaaat acctgctcaa ctacgcagac    180
ccgaaacaag gctgctggct ggacggcgtc accgtctacg gtgagatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca gtcggtcag cgccaagtac agcgttggcg gcagtatcga catcgtcaac    420
gtcagctcgg atatcactgt cggtttcagc agcaccgagg cctggtcgac gacccagacc    480
ttcacccaaa gcaccgagct ggccggtccg ggcaccttct tgtctatca ggtggtgttt    540 gtctacgcgc acaacgccac ctcggcgggc cggcagaatg gcaatgcctt tgcctatagc    600
aagacccagc aggtggattc gcggctcgat ctctactacc tgtcggccat cacccaggac    660
cgtacggtca tcgtcgagtc cagcaaggca atcaacccgc tggactggga taccgtgcag    720
```

```
cgcaacgtgc tgatcgagaa ctacaacccg gcctccaaca gtgggcactt ccgcttcgac      780
tggagcgcct acaacgatcc tcatcgccgc tac                                  813

<210> SEQ ID NO 35
<211> LENGTH: 813
<212> TYPE: DNA
<213> ORGANISM: artificial sequence
<220> FEATURE:
<223> OTHER INFORMATION: >IRDIG37126_D18Q_D75E (nucleotide sequence)

<400> SEQUENCE: 35
atgacgatca aggaagactt gagcaatcct caaagccatt cggtcgagct ccaacagttg       60
cacgtcgggg aagtctctgc acgcgaagcg ttgaccgcca acttcgccgg cagtttcgat      120
cagttcccga ccaaaagcgg cagcttcgag atcgacaaat acctgctcaa ctacgcagac      180
ccgaaacaag gctgctggct ggacggcgtc accgtctacg gtgaaatcta catcggcaag      240
cagaactggg gcacctacac gcgcccggtg ttcgcctacc tgcagcacac ggacaccatc      300
tcgattccgc agcaggtgac gcagaccaag agctaccagt tgagcaaagg ccacacccag      360
tcgttcacca agtcggtcag cgccaagtac agcgttggcg gcagtatcga catcgtcaac      420
gtcagctcgg atatcactgt cggtttcagc agcaccgagg cctggtcgac gacccagacc      480
ttcacccaaa gcaccgagct ggccggtccg ggcaccttct tgtctatca ggtggtgttt      540 gtctacgcgc acaacgccac ctcggcgggc cggcagaatg gcaatgcctt tgcctatagc      600
aagacccagc aggtggattc gcggctcgat ctctactacc tgtcggccat cacccaggac      660
cgtacggtca tcgtcgagtc cagcaaggca atcaacccgc tggactggga taccgtgcag      720
cgcaacgtgc tgatcgagaa ctacaacccg gcctccaaca gtgggcactt ccgcttcgac      780
tggagcgcct acaacgatcc tcatcgccgc tac                                  813

<210> SEQ ID NO 36
<211> LENGTH: 813
<212> TYPE: DNA
<213> ORGANISM: artificial sequence
<220> FEATURE:
<223> OTHER INFORMATION: >IRDIG37126_D18L_D75E (nucleotide sequence)

<400> SEQUENCE: 36
atgacgatca aggaagactt gagcaatcct caaagccatt cggtcgagct cctccagttg       60
cacgtcgggg aagtctctgc acgcgaagcg ttgaccgcca acttcgccgg cagtttcgat      120
cagttcccga ccaaaagcgg cagcttcgag atcgacaaat acctgctcaa ctacgcagac      180
ccgaaacaag gctgctggct ggacggcgtc accgtctacg gtgaaatcta catcggcaag      240
cagaactggg gcacctacac gcgcccggtg ttcgcctacc tgcagcacac ggacaccatc      300
tcgattccgc agcaggtgac gcagaccaag agctaccagt tgagcaaagg ccacacccag      360
tcgttcacca agtcggtcag cgccaagtac agcgttggcg gcagtatcga catcgtcaac      420
gtcagctcgg atatcactgt cggtttcagc agcaccgagg cctggtcgac gacccagacc      480
ttcacccaaa gcaccgagct ggccggtccg ggcaccttct tgtctatca ggtggtgttt      540 gtctacgcgc acaacgccac ctcggcgggc cggcagaatg gcaatgcctt tgcctatagc      600
aagacccagc aggtggattc gcggctcgat ctctactacc tgtcggccat cacccaggac      660
cgtacggtca tcgtcgagtc cagcaaggca atcaacccgc tggactggga taccgtgcag      720
cgcaacgtgc tgatcgagaa ctacaacccg gcctccaaca gtgggcactt ccgcttcgac      780
tggagcgcct acaacgatcc tcatcgccgc tac                                  813
```

```
<210> SEQ ID NO 37
<211> LENGTH: 7
<212> TYPE: PRT
<213> ORGANISM: artificial sequence
<220> FEATURE:
<223> OTHER INFORMATION: Protein motif identified for hemipteran active
      insect resistance proteins

<400> SEQUENCE: 37

Gln Leu His Val Gly Glu Val
1               5
```